US012797604B2

(12) United States Patent
Herrington et al.

(10) Patent No.: US 12,797,604 B2
(45) **Date of Patent: *Nov. 17, 2026**

(54) ARTIFICIAL RIGHT ATRIUM DESIGN FOR FAILING FONTANS

(71) Applicant: Children's Hospital Los Angeles, Los Angeles, CA (US)

(72) Inventors: Cynthia S. Herrington, Pasadena, CA (US); Jon David Menteer, Calabasas, CA (US); Sarah Badran, Rolling Hills Estates, CA (US); Heng Wei, Los Angeles, CA (US); Niema M Pahlevan, La Canada, CA (US)

(73) Assignee: CHILDREN'S HOSPITAL LOS ANGELES, Los Angeles, CA (US)

( * ) Notice: Subject to any disclaimer, the term of this patent is extended or adjusted under 35 U.S.C. 154(b) by 148 days.

This patent is subject to a terminal disclaimer.

(21) Appl. No.: 18/921,833

(22) Filed: Oct. 21, 2024

(65) Prior Publication Data

US 2025/0041585 A1 Feb. 6, 2025

Related U.S. Application Data

(63) Continuation of application No. 17/103,570, filed on Nov. 24, 2020, now Pat. No. 12,121,712.

(Continued)

(51) Int. Cl.

| | |
|---|---|
| ***A61M 60/50*** | (2021.01) |
| ***A61M 1/10*** | (2006.01) |
| ***A61M 60/258*** | (2021.01) |

(52) U.S. Cl.

CPC .......... *A61M 60/50* (2021.01); *A61M 60/258* (2021.01); *A61M 2205/02* (2013.01); *A61M 2210/125* (2013.01)

(58) Field of Classification Search

CPC ............ A61B 2576/023; A61B 5/0037; A61B 5/0044; A61B 5/02028; A61B 5/055;

(Continued)

(56) References Cited

U.S. PATENT DOCUMENTS

| | | | |
|---|---|---|---|
| 7,811,244 B2 | 10/2010 | Soerensen et al. |
| 8,449,443 B2 | 5/2013 | Rodefeld et al. |

(Continued)

OTHER PUBLICATIONS

Andrew L. Cheng et al., "Experimental investigation of the effect of non-Newtonian behavior of blood flow in the Fontan circulation", European Journal of Mechanics/ B Fluids, 68 (Year 2018), 184-192, 23 pages. doi: 10.1016/j.euromechflu.2017.12.009.

(Continued)

*Primary Examiner* — Jon Eric C Morales

(74) *Attorney, Agent, or Firm* — Mannava & Kang, P.C.

(57) ABSTRACT

An artificial chamber including a first conduit, a second conduit, a third conduit, and a wall defining a space; in which the first conduit and the second conduit are positioned opposite one another; in which the third conduit is opposite the wall; and in which the wall has a concave surface is disclosed. The chamber can be part of a system for providing pulmonary support. The system includes the chamber and a first pump connected to the third conduit, and connected to a fourth conduit; in which the chamber receives fluid via the first conduit and the second conduit, in which the first pump receives fluid from the chamber via the third conduit; and in which the fourth conduit transports fluid from the first pump to a first blood vessel. Methods of making a chamber and a system, and methods of using the chamber and system are also disclosed.

22 Claims, 14 Drawing Sheets

Related U.S. Application Data

Figure 1:
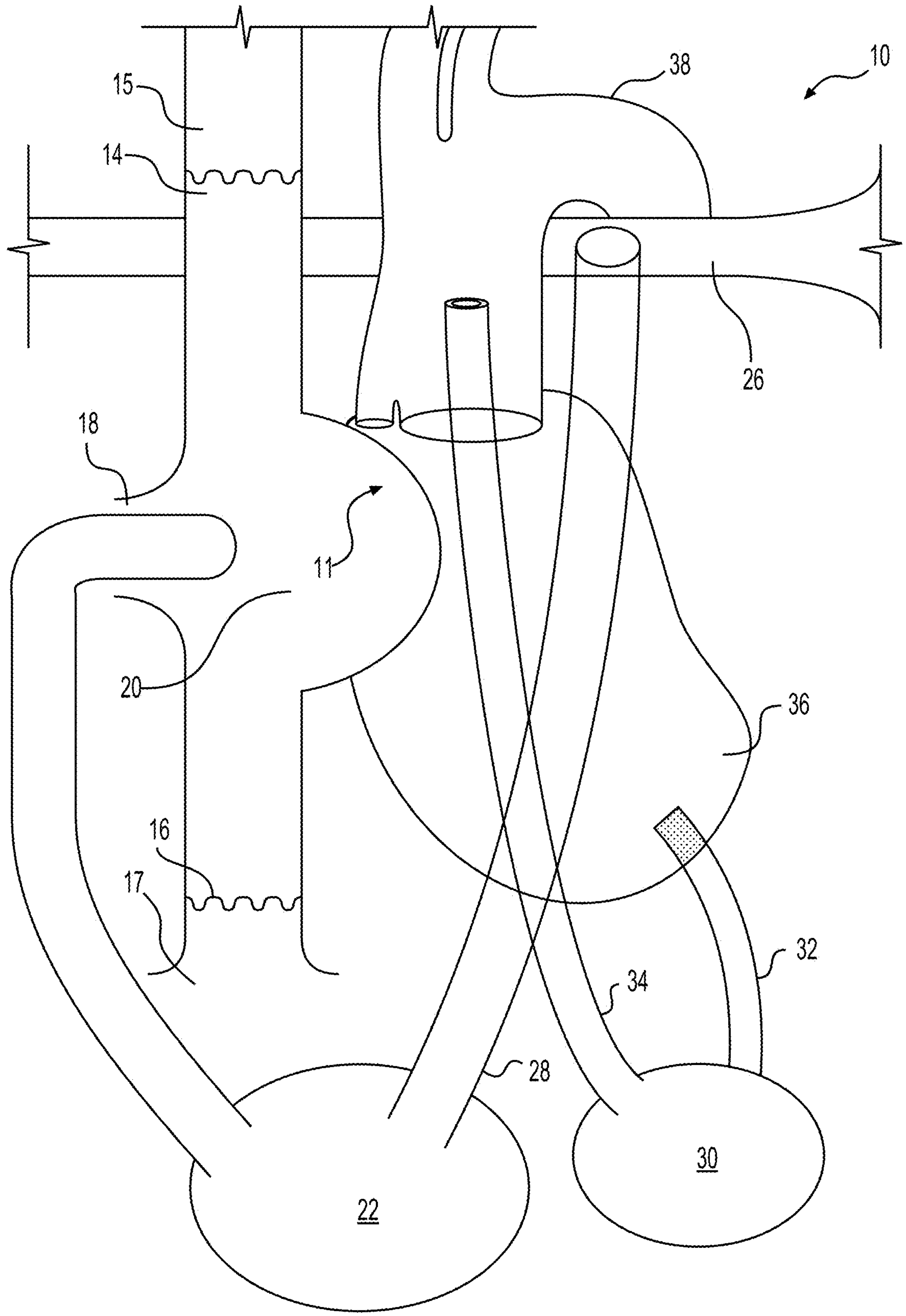

(60) Provisional application No. 62/939,992, filed on Nov. 25, 2019.

(58) Field of Classification Search
CPC ... A61B 5/1107; A61B 5/7207; A61B 5/7292; A61B 5/743; A61F 2/06; A61F 2002/068; A61F 2230/0054; A61F 2230/0056; A61F 2230/0058; A61M 2205/02; A61M 2210/125; A61M 60/148; A61M 60/178; A61M 60/205; A61M 60/247; A61M 60/258; A61M 60/35; A61M 60/50; A61M 60/857; A61M 60/869; G16H 30/20; G16H 30/40; G16H 40/63; G16H 50/20; G16H 50/30; Y10T 137/87249
See application file for complete search history.

(56) References Cited

U.S. PATENT DOCUMENTS

| | | | | |
|---|---|---|---|---|
| 9,227,002 | B1 | 1/2016 | Giridharan et al. | |
| 9,827,357 | B2 | 11/2017 | Rodefeld | |
| 12,121,712 | B2 * | 10/2024 | Herrington | A61M 60/50 |
| 2014/0275724 | A1 | 9/2014 | Wang et al. | |
| 2017/0311829 | A1 | 11/2017 | Beeckler et al. | |
| 2017/0311839 | A1 | 11/2017 | Osman | |
| 2018/0245243 | A1 | 8/2018 | Krieger et al. | |

OTHER PUBLICATIONS

Carlo Pace napoleone et al., "Ventricular assist device in a failing total cavopulmonary connection: a new step-by-step approach†", Interactive Cardio Vascular and Thoracic Surgery 26, (2018) 341-342.

Chin L. Poh et al., "Ventricular assist device support in patients with single ventricles: the Melbourne experience†", Interactive Cardio Vascular and Thoracic Surgery 25, (2017) 310-316.

Christopher C. Long et al., "Computation of residence time in the simulation of pulsatile ventricular assist devices", Computational Mechanics, Sep. 2013, 10 pages.

Heng Wei et al., "Fluid Dynamics Aspects of Artificial Right Atrium Design for Failing Fontans", Apr. 20, 2019, University of Southern California, 37 pages.

I. Halaweish et al., "Berlin heart ventricular assist as a long-term bridge to transplantation in a Fontan patient with failing single ventricle", Pediatr Transplantation Dec. 2015; 19(8):E193-1955. doi: 10.1111/petr.12607.

Jiun-Jr Wang et al., "Systemic venous circulation, Waves propagating on a windkessel: relation of arterial and venous windkessels to systemic vascular resistance", Published Online Jan. 1, 2006, 22 pages.

M. F. Snyder et al., "Computer Simulation Studies of the Venous Circulation", IEEE Transactions on Bio-Medical Engineering, vol. BME-16, No. 4, Oct. 1969, pp. 325-334.

Tracey Mackling et al., "Management of Single-Ventricle Patients With Berlin Heart EXCOR Ventricular Assist Device: Single-Center Experience", Thoughts and Progress, Artificial Organs vol. 36, No. 6, 2012, pp. 555-559.

* cited by examiner

ARTIFICIAL RIGHT ATRIUM DESIGN FOR FAILING FONTANS

RELATED APPLICATION

The present application is a continuation of U.S. Patent Application No. 17/103,570, filed on Nov. 24, 2020, now U.S. Pat. No. 12,121,712, which claims priority to U.S. Provisional Application No. 62/939,992, filed Nov. 25, 2019, the entire disclosures of both of which applications are hereby incorporated by reference.

FIELD OF THE INVENTION

The present invention relates generally to the field of cardiac medical devices and systems. In particular, the invention relates to a method and device to develop a new assist device for Fontan patients by creating a chamber, such as a synthetic right atrium, that minimizes blood particle component residence time, thereby preventing blood clotting and avoids and/or prevents over-pressurizing superior vena cava and inferior vena cava.

BACKGROUND OF THE INVENTION

The Fontan or Fontan/Kreutzer procedure is a palliative (not curative) surgical procedure used to ameliorate complex congenital heart defects, for example in young children. Exemplary heart defects addressed by the Fontan procedure include heart valve defects (tricuspid atresia, pulmonary atresia), abnormalities in pumping ability of the heart (hypoplastic left heart syndrome, hypoplastic right heart syndrome), and other complex congenital heart diseases where a bi-ventricular repair is not possible or contra-indicated (double inlet left ventricle, heterotaxy defects, double outlet right ventricle, etc.).

In the Fontan procedure, a surgically created junction is provided between the superior and inferior vena cava and the pulmonary artery (PA), and venous blood flow is diverted from the superior and inferior vena cava directly to the PA, bypassing the right ventricle of the heart. Following the procedure, oxygen-poor blood from the upper and lower body flows through the lungs without being pumped by the heart. In this manner, the blood flow into the lungs is driven only by central venous blood pressure. This corrects hypoxia, and leaves a single heart ventricle responsible for supplying blood to the body.

However, disadvantages and post-surgical complications are associated with the Fontan procedure. In the short term, pleural effusions (fluid build-up around the lungs) occur, requiring additional surgical interventions. In the long term, atrial scarring is associated with atrial flutter and atrial fibrillation, also requiring additional surgical intervention. Other long-term risks are associated with the procedure, such as protein-losing enteropathy and chronic renal insufficiency, although these latter risks are not yet fully quantified.

It is noted that a high central venous pressure is required to provide a satisfactory supply of blood to the lungs after the Fontan procedure. Immediately or even 2-5 years following the procedure, it is known that the surgically created Fontan circulation often fails due to that high venous pressure required to drive pulmonary circulation. Long term mortality following the Fontan procedure can be as high as 29.1%, characterized by catastrophic failure of circulation and death. The expected event-free survival rate following the Fontan procedure at one, ten, and twenty-five years following the procedure is 80.1%, 74.8%, and 53.6%, respectively. In early post-operative cases of failing Fontan circulation, the Fontan connection must be surgically taken down. In later post-operative cases, often the only remedy is heart transplantation.

In many post-operative cases, the patient's heart is in such a deteriorating state heart transplantation is not possible. In many cases, the surgeons have reversed the Fontan to create a right atrium to cannulate, but this results in massive bleeding, a poor chamber for cannulation, and the inability to support the patient.

What is needed is a system to ameliorate and/or treat at least one of the health problems discussed above in a patient in need thereof. For example, a system for providing pulmonary support to a patient can be provided.

SUMMARY OF THE INVENTION

In an aspect, there is disclosed an artificial chamber including a first conduit, a second conduit, a third conduit, and a wall defining a space; in which the first conduit and the second conduit are positioned opposite one another; in which the third conduit is opposite the wall; and in which the wall has a concave surface.

In another aspect, there is disclosed a system for providing pulmonary support comprising: a chamber defined by a first conduit, a second conduit, a third conduit, and a wall; and a first pump connected to the third conduit, and connected to a fourth conduit; wherein the chamber receives fluid via the first conduit and the second conduit, wherein the first pump receives fluid from the chamber via the third conduit; and wherein the fourth conduit transports fluid from the first pump to a first blood vessel.

In a further aspect, there is disclosed a method for using a system for providing pulmonary support in a patient in need thereof, comprising: attaching the system to at least one blood vessel, wherein the system includes a chamber defined by a first conduit, a second conduit, a third conduit, and a wall; and a first pump connected to the third conduit, and connected to a fourth conduit.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRA WINGS

Figure 4:
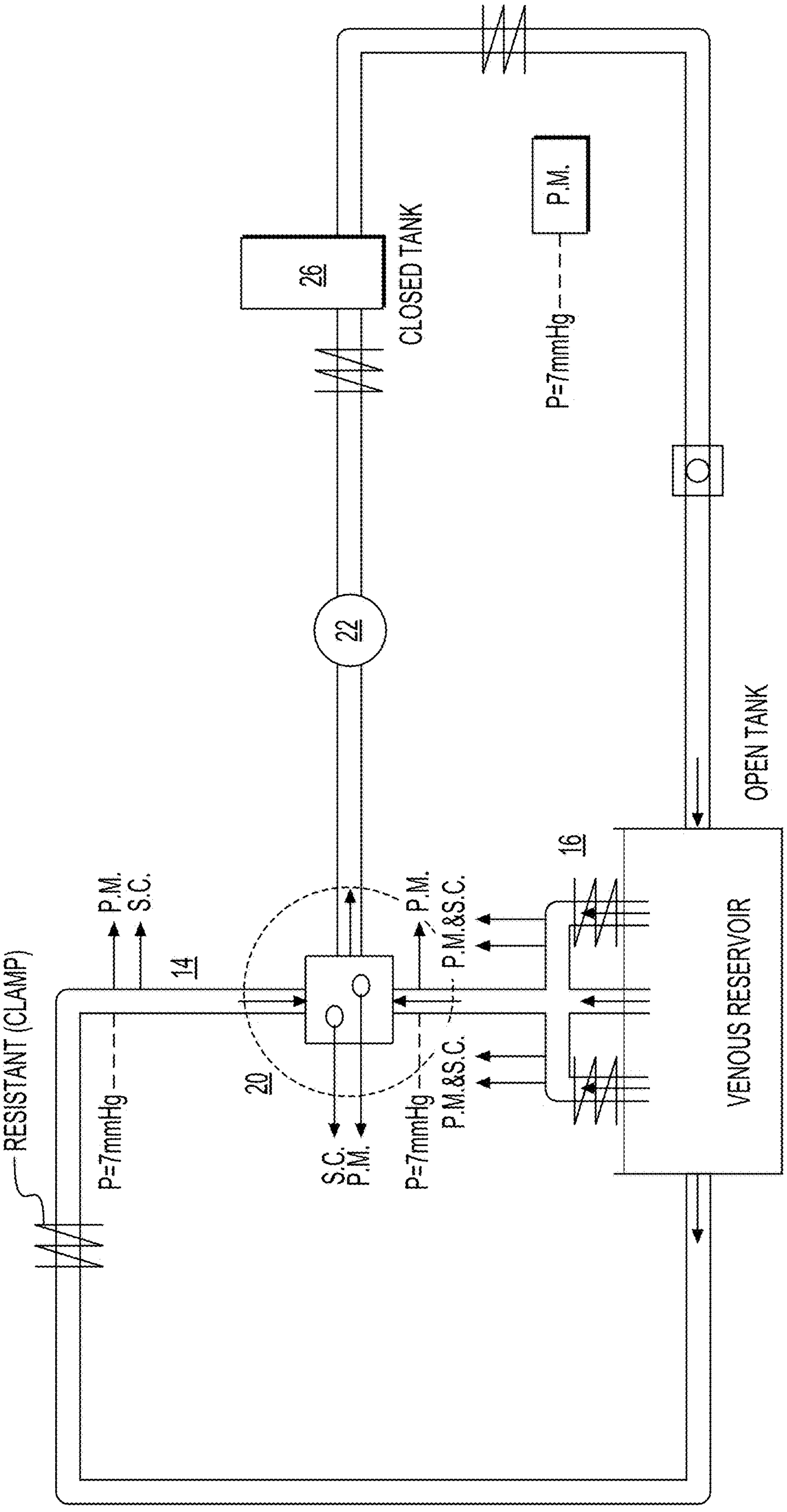

The present disclosure in its several aspects and embodiments can be more fully understood from the detailed description and the accompanying drawings, wherein:

FIG. 1 is a drawing of a system, according to an example of the present disclosure;

FIGS. 2A-G are two-dimensional drawings of a chamber, according to an example of the present disclosure;

FIGS. 3A-F are three-dimensional drawings of the chambers in FIGS. 2A-F, respectively;

FIG. 4 is a hydraulic circuit set-up to simulate the use of a system, according to an example of the present disclosure;

FIGS. 5A-J illustrate different experimental setup to illustrate the effects of using different types of chambers and pumps;

FIGS. 6A-J illustrate the pressures at the first conduit and the second conduit corresponding to each experimental setup of FIGS. 5A-J, according to an example of the present disclosure; and FIGS. 7A-F illustrate the simulated flow results corresponding to each of the FIGS. 2A-F and 3A-F, according to an example of the present disclosure.

Throughout this specification and figures like reference numbers identify like elements.

DETAILED DESCRIPTION OF THE INVENTION

It is to be understood that both the foregoing general description and the following detailed description are exemplary and explanatory only, and are intended to provide an explanation of various embodiments of the present teachings.

The present invention is directed to a system for providing pulmonary support to a patient in need thereof. The patient in need thereof can be failing from a prior Fontans procedure. In particular, the patient can be exhibiting at least one health problem chosen from pleural effusions, atrial scarring, atrial flutter, atrial fibrillation, protein-losing enteropathy, chronic renal insufficiency, and high central venous pressure. The system can stabilize a patient with a failing Fontans procedure by ameliorating and/or treating at least one of the health problems discussed above. The system can preserve compliance, i.e., prevent over-pressurizing blood vessels; and/or minimize particle residence time thereby preventing or reducing the likelihood of blood clots.

FIG. 1 illustrates a system 10 that can be surgically implanted into a patient in need thereof. The system includes a chamber 20 defined by a first conduit 14, a second conduit 16, a third conduit 18, and a wall 11; and a first pump 22 connected to the third conduit 18, and connected to a fourth conduit 28. The chamber 20 can receive fluid via the first conduit 14 and the second conduit 16. The first pump 22 can receive fluid from the chamber 20 via the third conduit 18. In an aspect, the first pump 22 can include an additional conduit so that the third conduit 18 connects to the additional conduit of the first pump 22. For example, the additional conduit can have an end that is smaller in diameter than a diameter of the third conduit so that the end of the additional conduit can fit within an end of the third conduit, as shown in FIG. 1. The fourth conduit 28 can transport fluid from the first pump 22 to a first blood vessel 26.

The system 10 can further include a second pump 30 connected to a fifth conduit 34, and connected to a sixth conduit 32. The fifth conduit 34 can transport fluid from a second blood vessel 38 to the second pump 30. The sixth conduit 32 can transport fluid from the second pump 22 to an organ 36.

The conduits (e.g., first, second, third, etc.) of the system 10 can transport a fluid between two members (e.g., chamber 20, and first pump 22) and/or a member (e.g., second pump 30) and a tissue, such as a blood vessel (e.g., first, second, third, etc.). The fluid can be blood. The conduits are numbered "first", "second", "third", etc. for ease of reference and it is not intended to limit the scope thereof. Each conduit 14, 16, 18, 28, 34, and 32 can include a first end and a second end. Each conduit 14, 16, 18, 28, 34, and 32 can include at least one valve located at the first end and/or the second end. As an example, the first conduit 14 can include a first end connected to the chamber 20, wherein the first end includes a valve (not shown), and the second end does not include a valve. As another example, the third conduit 18 can include a first end connected to the chamber 20 and including a first valve, and can include a second end connected to the first pump 22 and including second valve. In an aspect, each of the first conduit 14, the second conduit 16, and the third conduit 18 includes at least one valve. For example, each of the first conduit 14, the second conduit 16, and the third conduit 18 each have a first end including a valve.

The first conduit 14 can transport a fluid, such as blood, from a third blood vessel 15, such as a superior vena cava (SVC) 15 to the chamber 20. The second conduit 16 can transport a fluid, such as blood, from a fourth blood vessel 17, such as an inferior vena cava (IVC) 17. A blood vessel can be any vessel through which blood circulates. Non-limiting examples of blood vessels include artery, vein, capillary, arteriole, and venule.

The conduits 14, 16, 18, 28, 34, and 32 can be any size or shape to transport fluid. The conduits 14, 16, 18, 28, 34, and 32 can have a diameter, such as an inner diameter, that matches or substantially matches with a blood vessel, and/or an artificial implant. Each conduit 14, 16, 18, 28, 34, and 32 can have the same or different diameter, such as a diameter ranging from about 1.5 mm to about 35 mm, for example, from about 1.9 mm to about 24 mm, and as a further example, from about 2.1 mm to about 20 mm, including all points in between the ranges. Each of the first conduit 14, the second conduit 16, and the third conduit 18 can have the same diameter "D".

As discussed above, each conduit 14, 16, 18, 28, 34, and 32 can include a first end and a second end. The diameter of each conduit can be the same from the first end to the second end. The diameter of each end of the conduit can be different. For example, the diameter can increase or decrease along a length of the conduit so that the first end and the second end are different.

Each conduit 14, 16, 18, 28, 34, and 32 can include a length from the first end to the second end. The length of each conduit 14, 16, 18, 28, 34, and 32 can be the same or different. Prior to insertion of the chamber 20 into a patient in need thereof, the length of each conduit can have an initial length. The initial length of each conduit can be shortened during insertion of the chamber.

In an aspect, a chamber 20 including the first, second, and third conduits can have standard sizes for each component. The standard sizes can be designed based upon a imaging data from patients. For example, patients age 2 years old could use a chamber 20 having first, second, and third conduits having a first standard size; and patients age 4 years old could use a chamber 20 having first, second, and third conduits having a second standard size. It is envisioned that some patients may not "fit" standard sizes and would require a custom-made chamber 20. A process for designing a chamber 20 is discussed more fully below.

In an example, the conduits 14, 16, 18, 28, 34, and 32 can be made of the same material as the chamber 20. In another example, the conduits 14, 16, 18, 28, 34, and 32 can be made of a different material from the chamber 20. Additionally, the conduits 14, 16, 18, 28, 34, and 32 can be made of the same material or can be made from a different material. For example, conduits 14, 16 can be the same material as conduit 18. As another example, conduits 14, 16 can be a different material from conduit 18.

The chamber 20 can be any size or shape to receive fluid. In an aspect, the chamber can be configured to mimic a right atrium of a heart.

The chamber 20 can be formed of any material. In an example, the chamber 20 can be made of a rigid material. In another example, the chamber 20 can be made of non-rigid (i.e., compliant) material. The chamber 20 can be made of a material that can withstand a pressure of from about 0 mm Hg to about 10 mm Hg, such as a pressure of from about 1 mm Hg to about 9 mm Hg, and for example, from about 2 mm Hg to about 8 mm Hg. Non-limiting examples of suitable materials include polyester, polytetrafluoroethylene, silicon, latex, any deformable FDA-approved biocompatible material, and a combination thereof. Moreover, the chamber 20 can be made of a material that can expand or contract (in volume) to about 5% to about 95%, such as from about 10% to about 90%, and as an example, from about 20% to about 85%, relative to an original size of the material. In an aspect, the chamber of the graft expands from about 0.5% or less to about 50% or more in volume.

The chamber 20 can include a coating on an exterior surface and/or an interior surface of the chamber 20. Such a coating can include an antibiotic coating or an anti-coagulant coating. The coating can include any drug-eluting material and/or matrix, for example, to facilitate the release a drug into a patient in need thereof. The drug can be any drug that does interfere with the operation of the chamber 20.

The chamber 20 can also include at least one external ring. For example, a first conduit 14 can include an external ring on at least one of the first end and the second end. The external ring can provide support. The external ring can prevent or inhibit external compression and distortion of each conduit and/or the chamber 20.

FIGS. 2A-G and FIGS. 3A-F illustrate a few exemplary shapes of chamber 20. FIGS. 2A-F illustrate a chamber with two-dimensional modeling, and FIGS. 3A-F illustrate the same chambers with three-dimensional modeling, respectively. As shown, in FIGS. 2A-G the chamber 20 can be defined by the first conduit 14, the second conduit 16, the third conduit 18, and a wall 11. In an aspect, the first conduit 14 can be oppositely-oriented with respect to the second conduit 16. In another aspect, the third conduit 18 can be oppositely-oriented with respect to the wall 11. The chamber 20 can be configured to preserve compliance, such as by preventing over-pressurizing from the first conduit 14 and the second conduit 16. The chamber 20 can also be configured to minimize particle residency time, which can reduce and/or prevent blood clotting.

With regard to FIGS. 2A-G and FIGS. 3A-F, the first conduit 14, the second conduit 16, and the third conduit 18 have the same diameter D. It should be noted that the diameter D of each conduit can be the same or different.

Figure 2A:
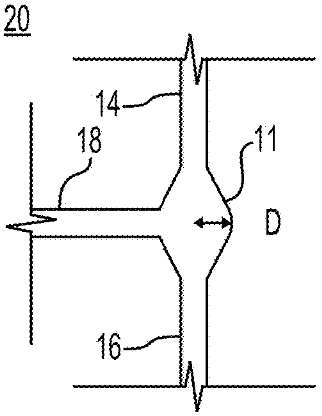
Figure 2B:
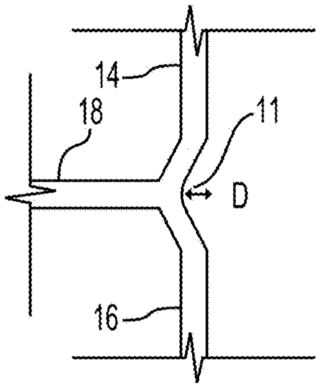
Figure 2C:
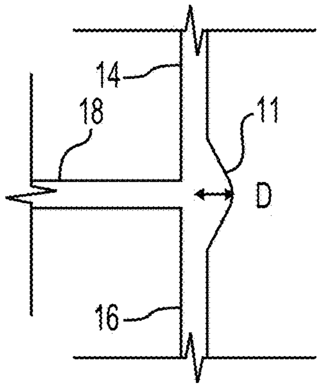
Figure 2D:
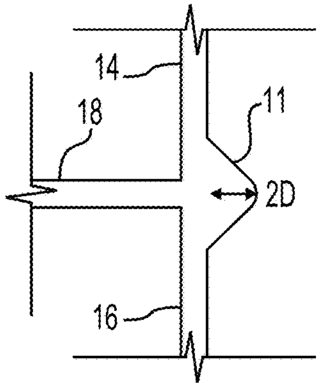
Figure 2E:
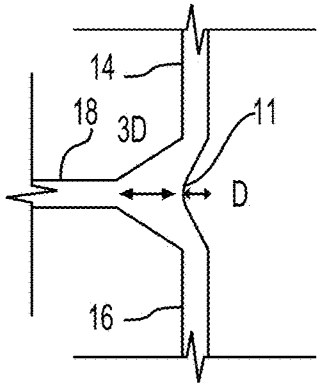
Figure 2F:
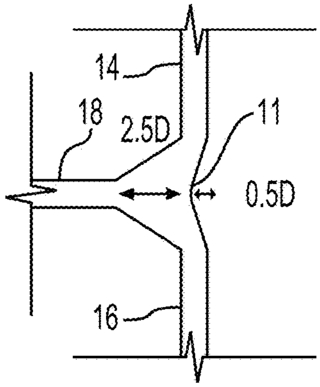
Figure 2G:
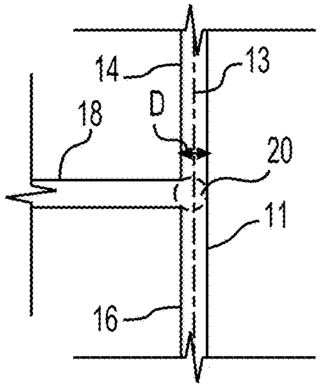

As shown in FIG. 2G, the simplest shape of the chamber 20 can include the first conduit 14, the second conduit 16, and the third conduit 18 each having the same diameter D, so that the chamber has a width that is also D. The chamber 20 is defined by the conduits 14, 16, 18, and is illustrated by the dashed line in FIG. 2G. The third conduit 18 can be orthogonal to the first conduit 14 and the second conduit 16 to form a T-shaped chamber 20, with the wall 11 as a linear extension of the first conduit 14 and the second conduit 16. FIG. 2G illustrates a baseline size and shape from which the chamber 20 can be configured. As explained in more detail below, the size and shape of the chamber 20 can be altered by increasing or decreasing the wall 11 and/or the connection surface of the third conduit 18 from an axis 13 to provide a convex or concave surface.

In an aspect, the wall 11 of the chamber 20 can be increased or decreased a predetermined width relative to the diameter D of the first conduit 14 and/or the second conduit 16. In this manner, the wall 11 of the chamber 20 can have a convex surface or a concave surface. For example, as shown in FIGS. 2A and C, the wall 11 can be increased a width that is the same as the diameter D of the conduits 14, 16 so that the wall 11 has a convex surface. As another example, the wall 11 can be increased by a different width relative to the diameter D of the first conduit 14 and the second conduit 16 to provide a convex surface, such as 2D, as shown in FIG. 2D. In an aspect, the wall 11 can have a convex surface that is increased about 0.1D to about 4D, for example, from about 0.25D to about 3.5 D, and as a further example, from about D to about 3D, relative to an initial diameter D of the first conduit 14 and the second conduit 16. It should be understood that 4D means 4 times the diameter D of the first conduit 14 when each conduit of the chamber 20 has the same diameter D. As discussed herein, the chamber 20 can have a standard size or can be custom designed.

In another aspect, as shown in FIGS. 2B, E, and F the wall 11 can be decreased a width relative to the diameter D of the conduits 14, 16 so that the wall 11 has a concave surface. For example, the wall 11 can be decreased a width that is the same as the diameter D of the conduits 14, 16 so that the wall 11 has a convex surface, as shown in FIGS. 2B and E. As another example, the wall 11 can be decreased to any a different width relative to the diameter D of the first conduit 14 and the second conduit 16 to provide a concave surface, such as 0.5D, as shown in FIG. 2F. In an aspect, the wall 11 can have a concave surface that is decreased about 0.1D to about 4D, for example, from about 0.25D to about 3.5 D, and as a further example, from about D to about 3D, relative to an initial diameter D of the first conduit 14.

Referring back to FIG. 2G, the third conduit 18 can be positioned orthogonal to the first conduit 14 and the second conduit 16. See, e.g., FIGS. 2C and D. In another aspect, the third conduit 18 can be positioned on a convex surface, as shown in FIGS. 2A, B, E, and F, opposite wall 11. For example, the third conduit 18 can be positioned at an apex of the convex surface. The third conduit 18 can be positioned on a convex surface, opposite wall 11, in which the convex surface is formed by an increased width relative to the diameter D of the first conduit 14 and/or the second conduit 16. For example, the third conduit 18 can be positioned on the convex surface having a width the same as the diameter D of the conduits 14, 16, as shown in FIGS. 2A and B. As another example, the third conduit 18 can be positioned on a convex surface that can be increased by a different width relative to the diameter D of the first conduit 14 and the second conduit 16, such as 2.5D, as shown in FIGS. 2E and F. In an aspect, the third conduit 18 can be positioned on a convex surface that is increased about 0.1D to about 4D, for example, from about 0.25D to about 3.5 D, and as a further example, from about D to about 3D, relative to an initial diameter D of the first conduit 14 and the second conduit 16. In an aspect, the chamber can include at least one convex surface.

Figure 3A:
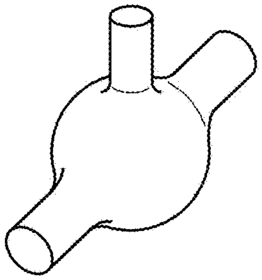
Figure 3B:
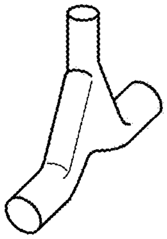
Figure 3C:
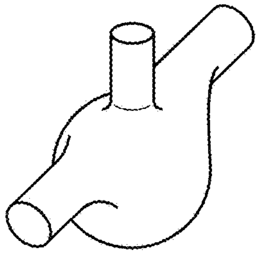
Figure 3D:
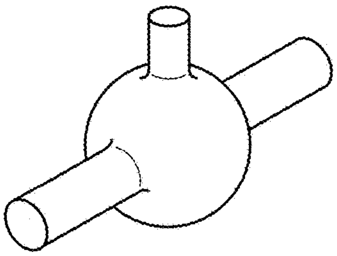
Figure 3E:
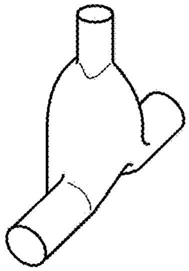
Figure 3F:
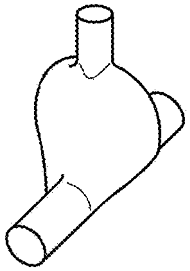

In an aspect, the chamber 20 can include a third conduit 18 positioned on a convex surface and a wall 11 having a concave surface, as shown in FIGS. 2B, E, and F. In an example as shown in FIGS. 2B and 3B, both the convex surface and the concave surface can include the same width relative to the diameter D, which is the same diameter as the diameter of the inlets 14, 16 and outlet 18. In another example, as shown in FIG. 2E the convex surface can include a width that is different than the diameter D the diameter of the inlets 14, 16 and outlet 18, and the wall 11 can have a concave surface with a width that is the same relative to the diameter D. In yet another example, as shown in FIG. 2F, both the third conduit 18 positioned on a convex surface and the concave surface of wall 11 can include a different width relative to the diameter D of the conduits 14, 16. For example, the third conduit 18 can be present on a convex surface that includes a width that is about 2.5 times the diameter of the conduits 14, 16. Additionally, the concave surface of wall 11 can include a width that is about 0.5 times the diameter of the conduits 14, 16.

The chamber 20 can include a convex surface and a concave surface so that the shape of the chamber 20 mimics the shape of the right atrium. A ratio of the width of the convex surface to the concave surface can be from about 0.0:4 to about 4:0.0, such as from about 0.5:3 to about 3:0.5. A volume of the chamber 20 can include a volume from about 0.1 cc to about 150 cc, such as from about 2 cc to about 100 cc, for example from about 5 cc to about 50 cc. The chamber 20 can have a standard volume based upon standard sizes from a majority of patients sizes/ages. The chamber 20 can also have a custom designed volume based upon a patient-specific condition. In an example, the ratio of a diameter of the convex area to the concave area the can be from about 0.0:4 to about 4:0.0, such as from about 0.5:3 to about 3:0.5. Moreover, the volume of the chamber 20 may include a volume of from about 0 cc to about 50 cc, such as from about 23 cc to about 41 cc. In an example, the chamber includes a volume of from about 1 cc (1 cc=1 ml) to about 110 cc (ml).

The first pump 22 and the second pump 30 can each be a pressure-source pump (i.e., flow drops as resistance increases) or a flow-source pump (i.e., flow does not drop with resistance increases).

Fluid, such as reduced or low-oxygen blood (AKA blue blood), from blood vessels 15, 17 can come together in chamber 20 via first conduit 14 and second conduit 16. The first pump 22 can pump the low-oxygen blood from the chamber 20 via third conduit 18 to a blood vessel 26, which can transport the fluid to the lungs for oxygenation. In an embodiment, the blood vessel 26 is the pulmonary artery.

In an example, if the left atrium and the left ventricle of the organ 36 are functional, then, the organ 36 can pump oxygenated fluid into the body via blood vessel 38. In another example, as shown in FIG. 1, if the left atrium and/or the left ventricle are not functioning properly, a second pump 30 can be utilized to pump the oxygenated blood into the body. In this example, the second pump 30 can include a conduit 32, which receives the oxygenated blood through one of pulmonary veins, left atrium, and/or left ventricle. The second pump 30 can then pump the oxygenated blood into the blood vessel 38, such as the aorta, via the conduit 34.

There is disclosed a method for using a system for providing pulmonary support in a patient in need thereof, comprising attaching the system to at least one blood vessel, wherein the system includes a chamber 20 defined by a first conduit 14, a second conduit 16, a third conduit 18, and a wall 11; and a first pump 22 connected to the third conduit 18, and connected to a fourth conduit 28. The first conduit can be attached to a third blood vessel 15. The second conduit 16 can be attached to a fourth blood vessel 17. The fourth conduit 28 can be attached to a first blood vessel 26, such as a pulmonary artery. The method can also include attaching a second pump 30. In particular, a sixth conduit 32 of the second pump 30 can be attached to an organ 36, such as the heart (e.g., left atrium, left ventricle), and/or pulmonary veins, as described above with respect to FIG. 1. Additionally, a fifth conduit 34 of the second pump 30 can be attached to a second blood vessel 38, such as an aorta. In an aspect, the method can provide cavopulmonary assistance to failing Fontan circulation and includes replacing a Fontan graft used in a Fontan procedure with a system of the present application.

There is also disclosed a method of making a chamber for a patient in need thereof, comprising imaging the patient to obtain measurements; determining a long axis plane for the chamber; and making the chamber 20. The imaging can be any three-dimensional and/or two-dimensional imaging of the patient. The step of determining a long axis plane can be determined using computational fluid dynamic (CFD) tools. The long axis plane is a cross-section with two flow inputs, for example, the first and second conduits 14, 16; and at least one output flow, for example, the third conduit 18. The long axis plane should minimize particle residence time (PRT) based upon a patient's anatomical data obtained from the imaging.

Using an appropriate material, such as a biocompatible material, a chamber 20 can be made. A patient-specific three-dimensional geometry of the chamber 20 can be created with the determined long axis plane. The chamber 20 can fit the patient's geometry and can preserve compliance using the blood vessel diameters of the patient and physiological data (e.g., volume flow rates). The chamber 20 can be made using three-dimensional printing and/or any known method for fabricating a medical implant.

The method can further include testing hemodynamic responses of the chamber 20. Non-limiting examples of hemodynamic responses include pressure, flow, collapse. The testing can be performed in physiologically accurate in-vitro systems.

The method can further include making a chamber 20 with a mechanical material property, such as elasticity, viscoelasticity) and three-dimensional geometry using an FDA-approved biocompatible material.

The chamber 20 can be surgically implanted into the patient.

Examples

FIG. 4 is an example of a hydraulic circuit used to evaluate the compliance and particle resident time of an exemplary system 10. The chamber 20 was designed to function as an artificial right atrium and is represented by the square in the center of the set-up. The first conduit 14 and the second conduit 16 are illustrated as the two inlet flows into the chamber 20. The third conduit 18 (not shown) is an outlet flow from the chamber 20 to the first pump 22, which then goes to the first blood vessel 26 and the lung (labeled as "closed tank"). A syringe was used to add compliance (S.C.)" to the system 10 at various locations. Systemic the rest of circulatory circuit after the lung was simplified and simulated with a tube and resistance. Fluid flow was measured (Q) before the fluid entered the venous reservoir. Pressure was measured (P.M.) at various location in the circuits such as first conduit 14, second conduit 16, and inside the chamber 20. Pressure was measured using a Millar System, PCU-200 Dual Channel Pressure Control Unit and Mikro-Cath™ Disposable Pressure Catheter. Fluid Flow was measured using a Transonic Systems Inc. T208 volume flow meter. The stagnation pressure was 7 mm Hg, the pulsatile mode was 60 bpm, and the cardiac output was fixed to be 2 L/min. Three separate sets of experiments were run: (a) with a rigid chamber with compliance (pressure source pump), Examples 1-6; (b) a piston pump, Examples 7-8; and (c) with a compliant chamber, Examples 9-10.

With regard to Examples 1-6 below, a rigid chamber with added compliance was studied by using a syringe at the following locations: chamber 20—0.1 ml/mmHg/kg; first conduit 14—0.08 ml/mmHg/kg; and second conduit 16—0.32 ml/mmHg/kg.

Figure 5A:
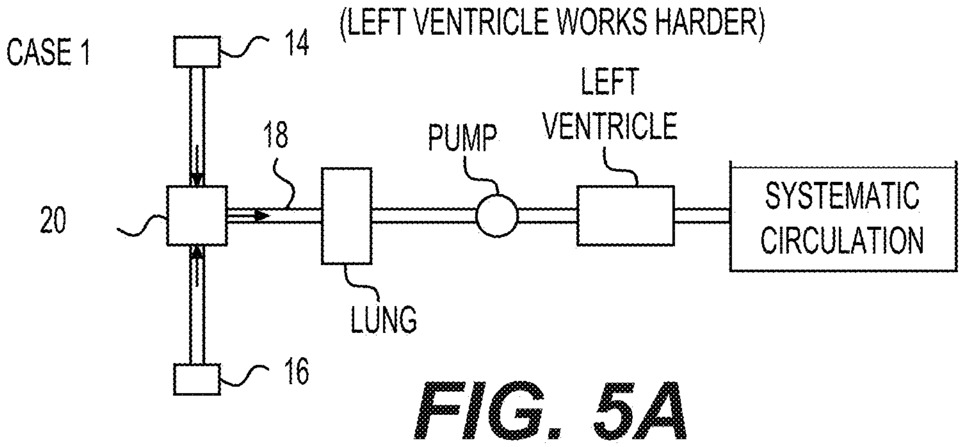

Example 1 (Comparative)—As shown in FIG. 5A, case 1 was a system 10 including a chamber 20 with a first conduit 14, a second conduit 16, and a third conduit 16 (orthogonal to the conduits 14, 16) that was directly linked to the lung. From the lung, the fluid flow continued to the first pump 22, which then returned the fluid to the venous reservoir and then back to the chamber 20. The chamber 20 is a rigid chamber made of glass.

Figure 5B:
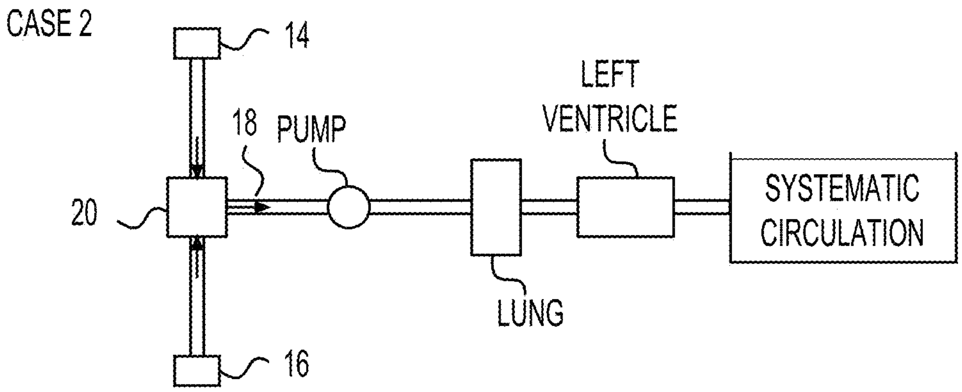

Example 2—As shown in FIG. 5B, case 2 was a system 10 including a chamber 20 with a first conduit 14, a second conduit 16, and a third conduit 16 (orthogonal to the conduits 14, 16) that was connected to the first pump 22. The first pump 22 then circulated the blood into the lungs. The chamber 20 is a rigid chamber made of glass.

Figure 5C:
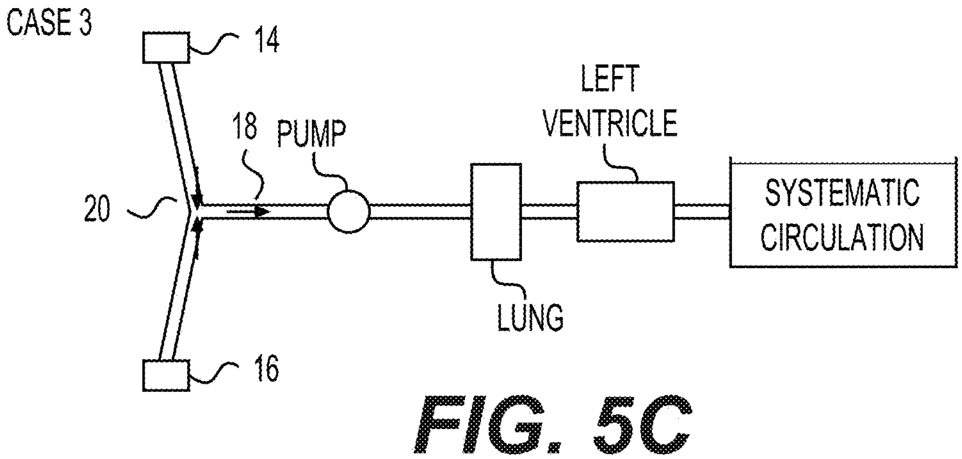

Example 3—As shown in FIG. 5C, case 3 was a system 10 including a chamber 20 with a first conduit 14, a second conduit 16, and a third conduit 16 (y-connector to the conduits 14, 16). The y-connector was used to simulate a chamber 20 having a wall 11 with a concave surface and the third conduit 16 positioned on a convex surface. The first pump 22 then circulated the blood into the lungs. The chamber 20 is a rigid chamber made of glass.

Figure 5D:
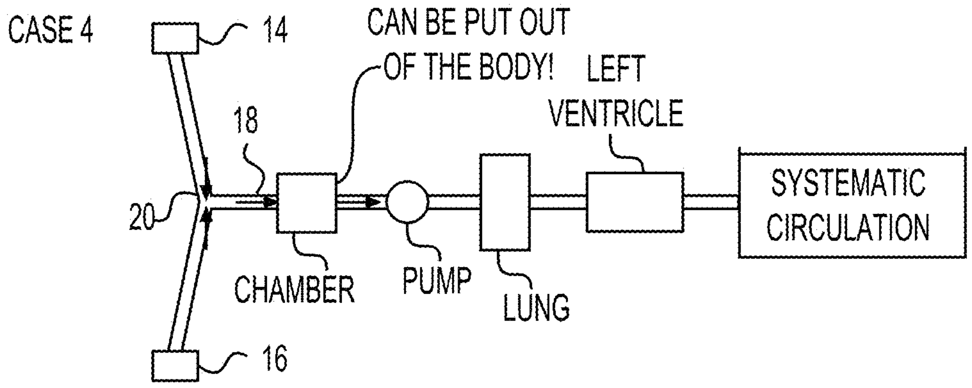

Example 4 (Comparative)—As shown in FIG. 5D, case 4 was a system 10 in which the first conduit 14 and the second conduit 15 merged together before they entered the chamber 20, i.e., a single inlet and a single outlet. The third conduit 18 exited the chamber 20 and connected to the first pump 22. The first pump 22 then circulated the blood into the lungs. The chamber 20 is a rigid chamber made of glass.

Figure 5E:
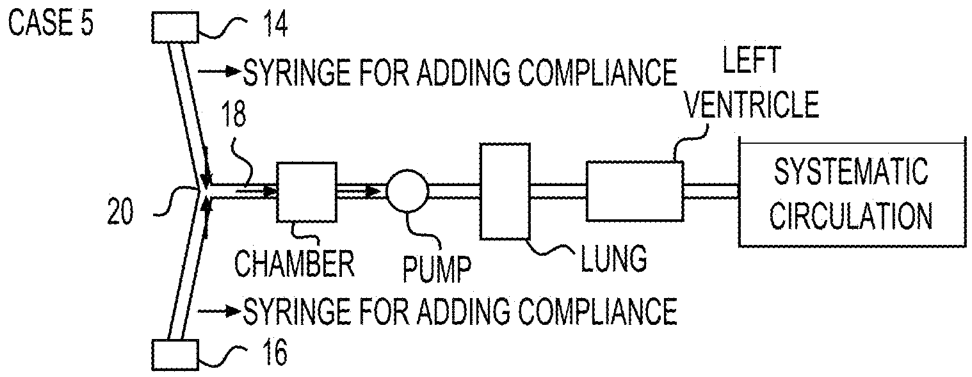

Example 5 (Comparative)—As shown in FIG. 5E, case 5 was similar to case 4, but also included a syringe on each of the first conduit 14 and the second conduit 16 to simulate additional external compliance to the system 10. Case 5 included a pressure-source pump. In a pressure-source pump, when the vasculature resistance increases, the pressure generated by the pump will remain the same, but the cardiac output will decrease. The chamber 20 is a rigid chamber made of glass.

Figure 5F:
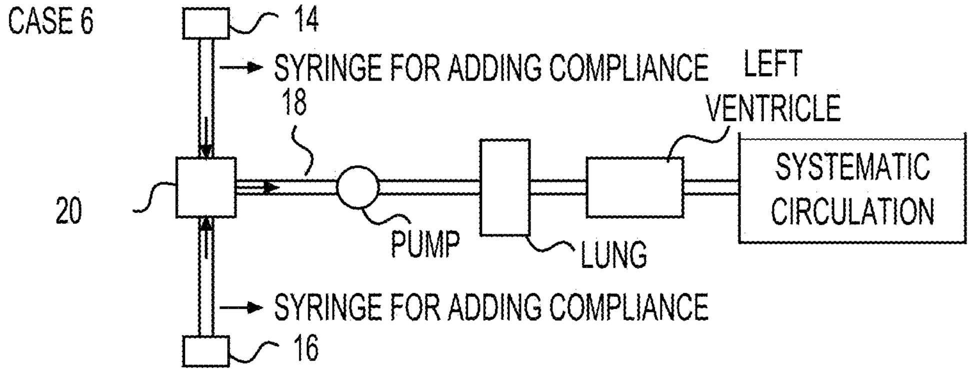

Example 6—As shown in FIG. 5F, case 6 was similar to case 2, but also included a syringe on each of the first conduit 14 and the second conduit 16 to simulate additional external compliance to the system 10.

Figure 5G:
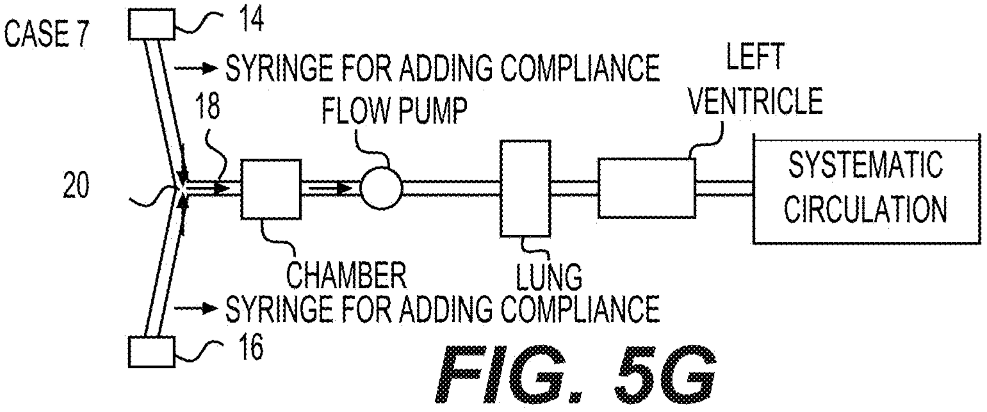

Example 7 (Comparative)—As shown in FIG. 5G, case 7 is similar to case 5 except that case 7 utilized a flow-source pump (e.g. piston-pump). In a flow-source pump, when the vasculature resistance increases, the cardiac output will remain unchanged and the pressure will increase. The chamber 20 is a rigid chamber made of glass.

Figure 5H:
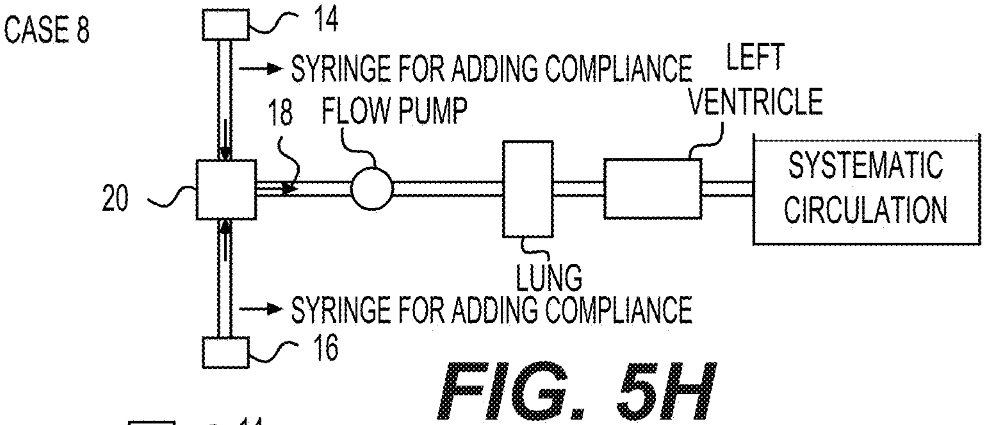

Example 8—As shown in FIG. 5H, case 8 is similar to case 6 where the pump is a strictly a flow-source pump (e.g. piston-pump).

Figure 5I:
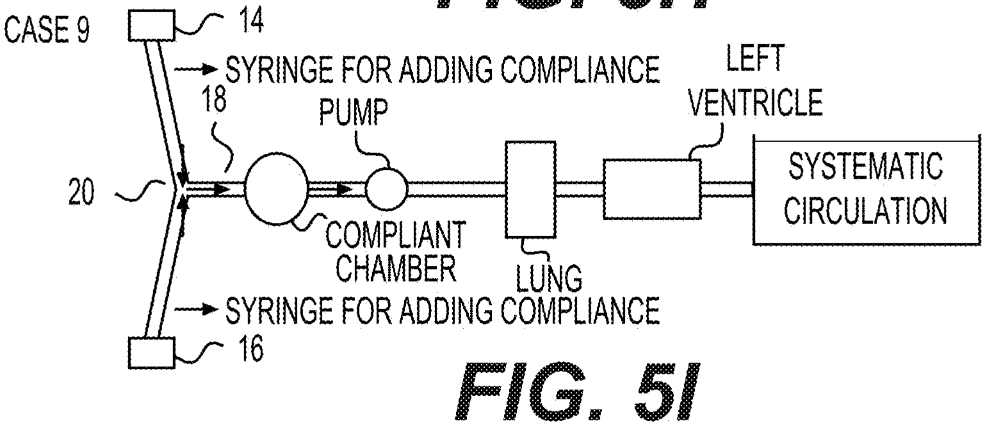

Example 9 (Comparative)—As shown in FIG. 5I, case 9 is similar to case 5 where the chamber 20 was composed of a non-rigid material, such as silicon or latex.

Figure 5J:
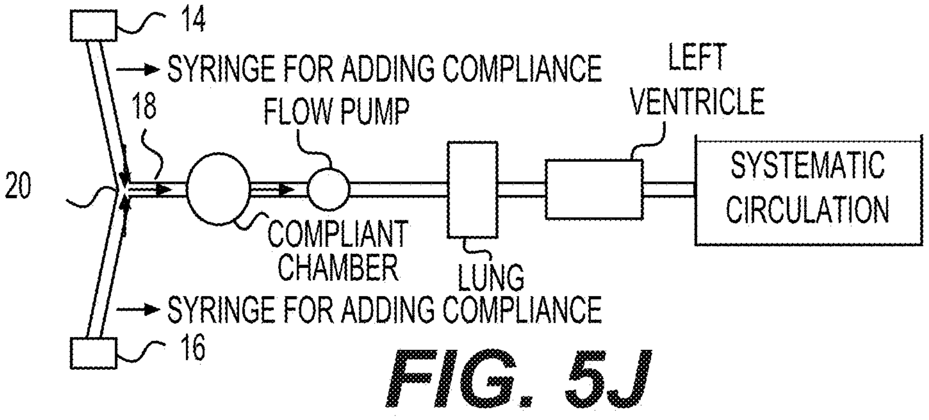
Figure 6B:
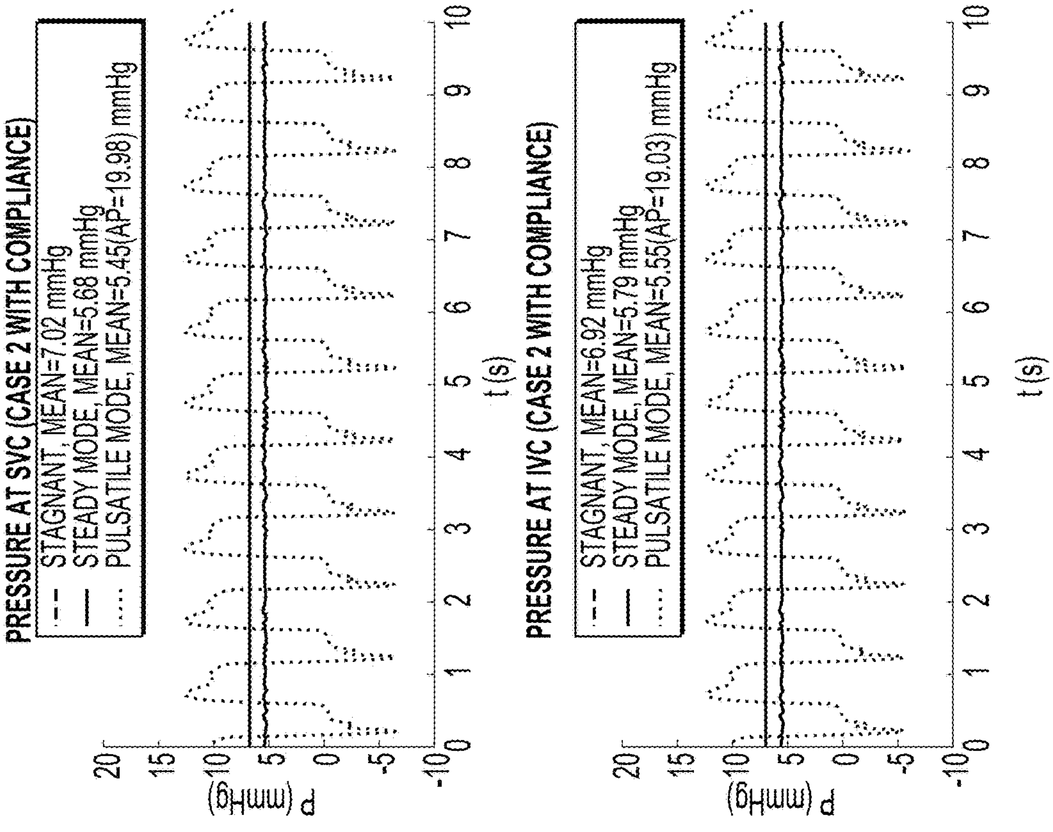
Figure 6A:
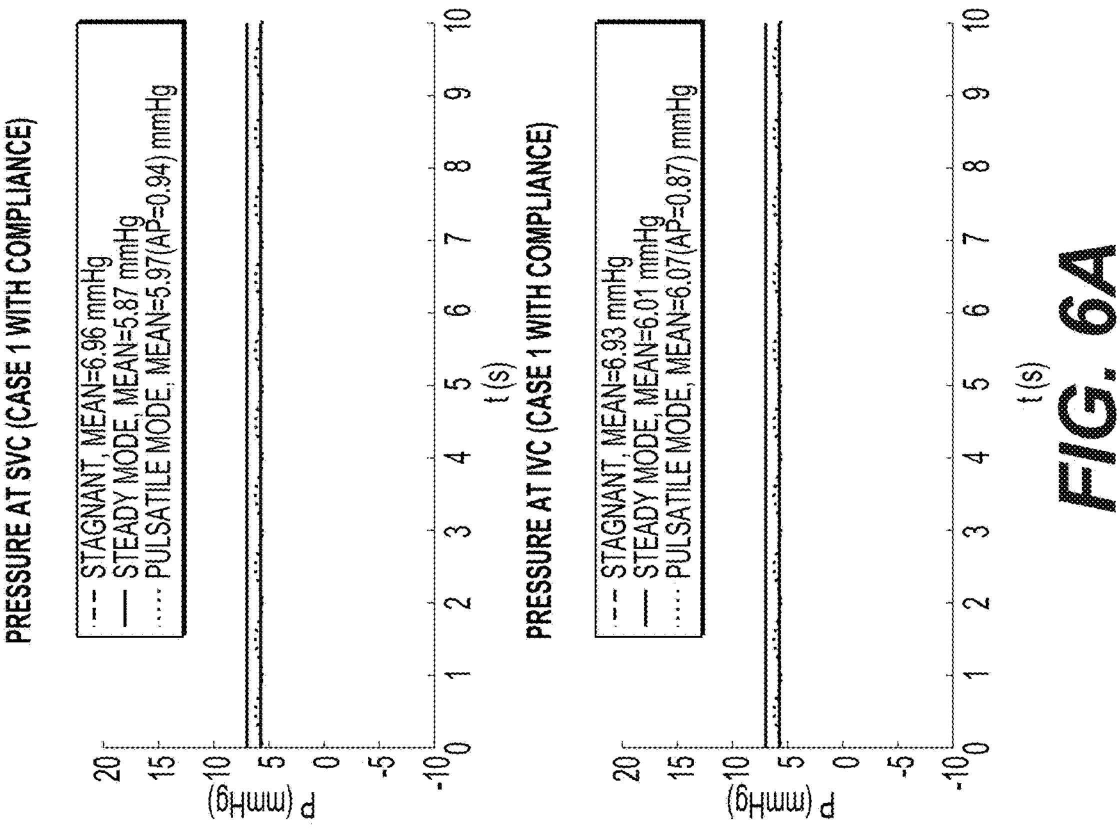
Figure 6C:
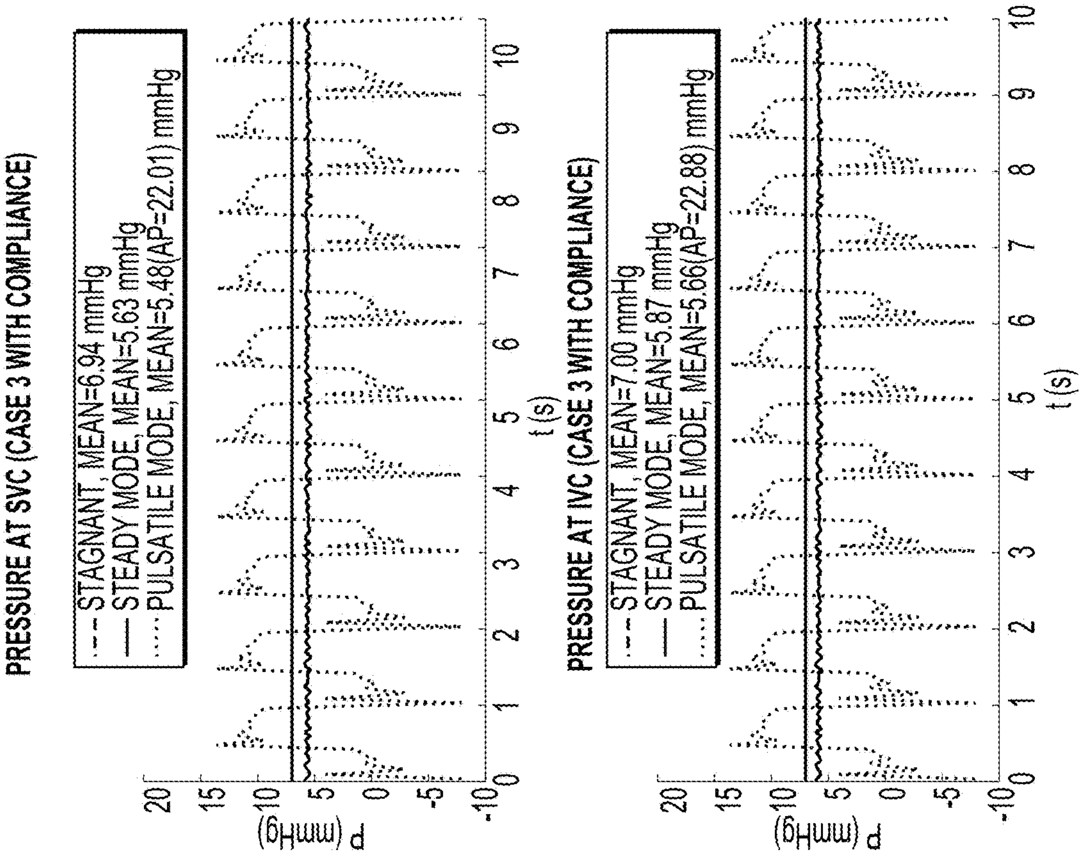
Figure 6D:
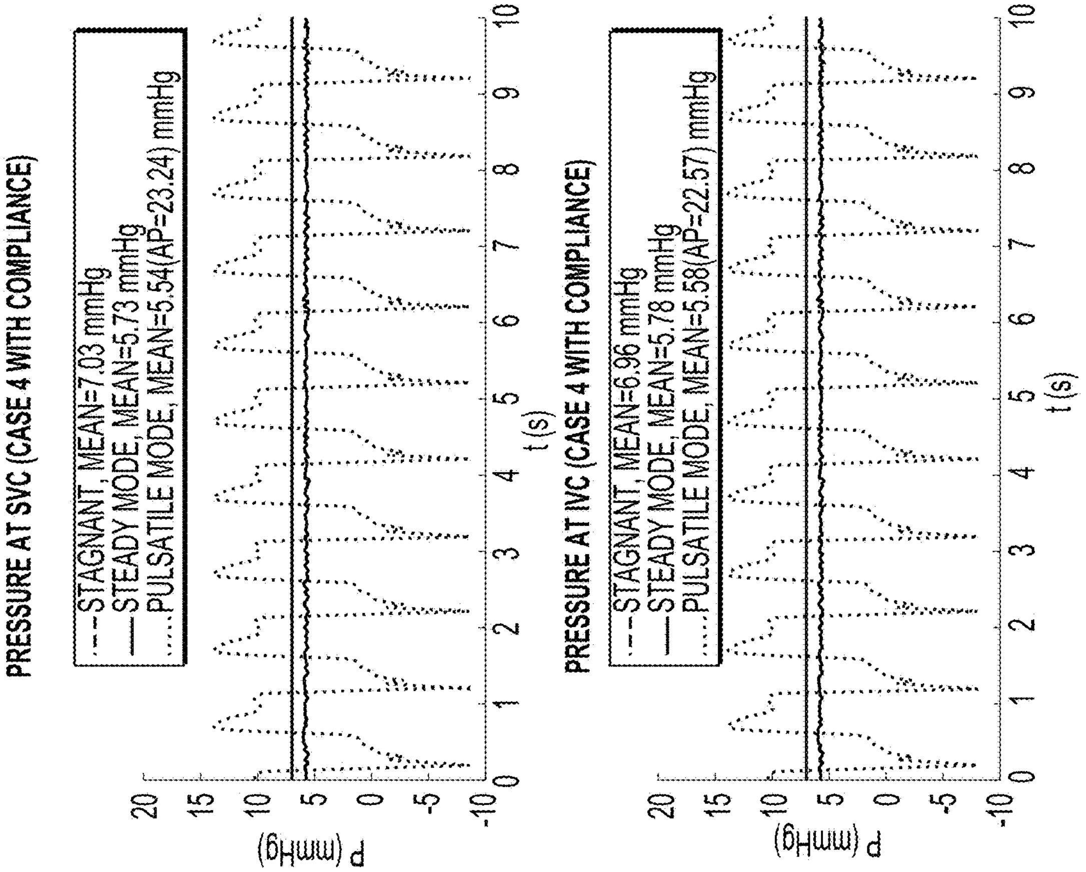
Figure 6E:
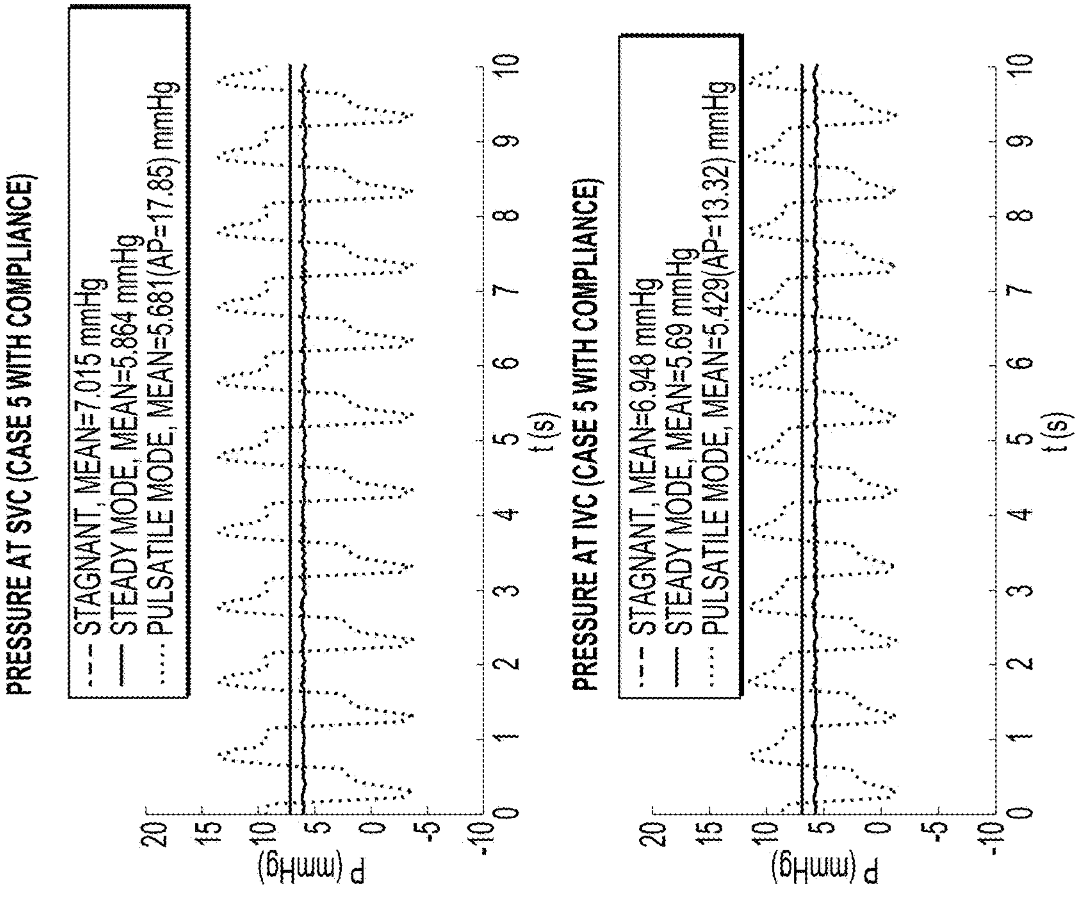
Figure 6F:
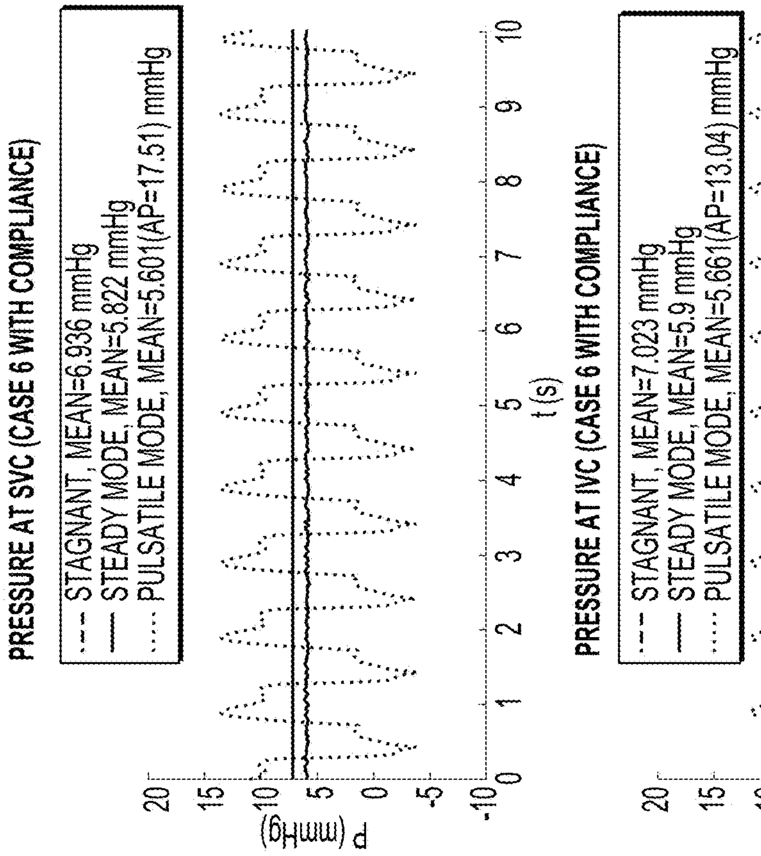
Figure 6G:
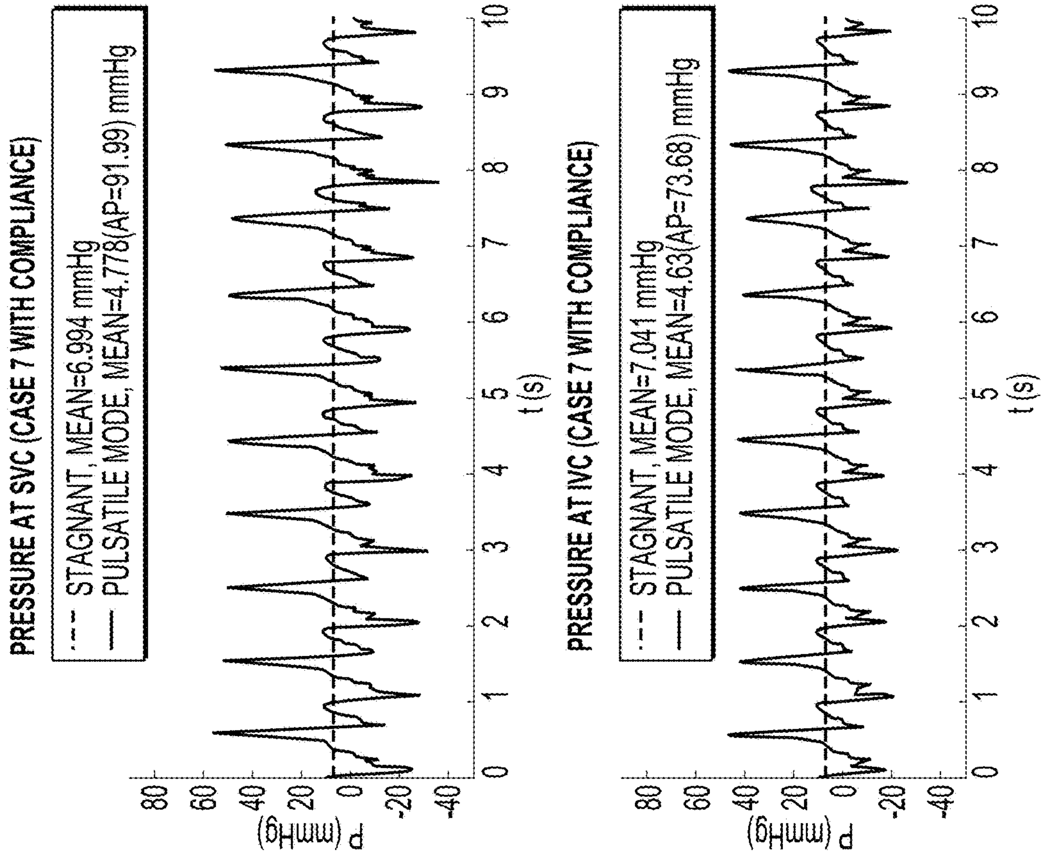
Figure 6H:
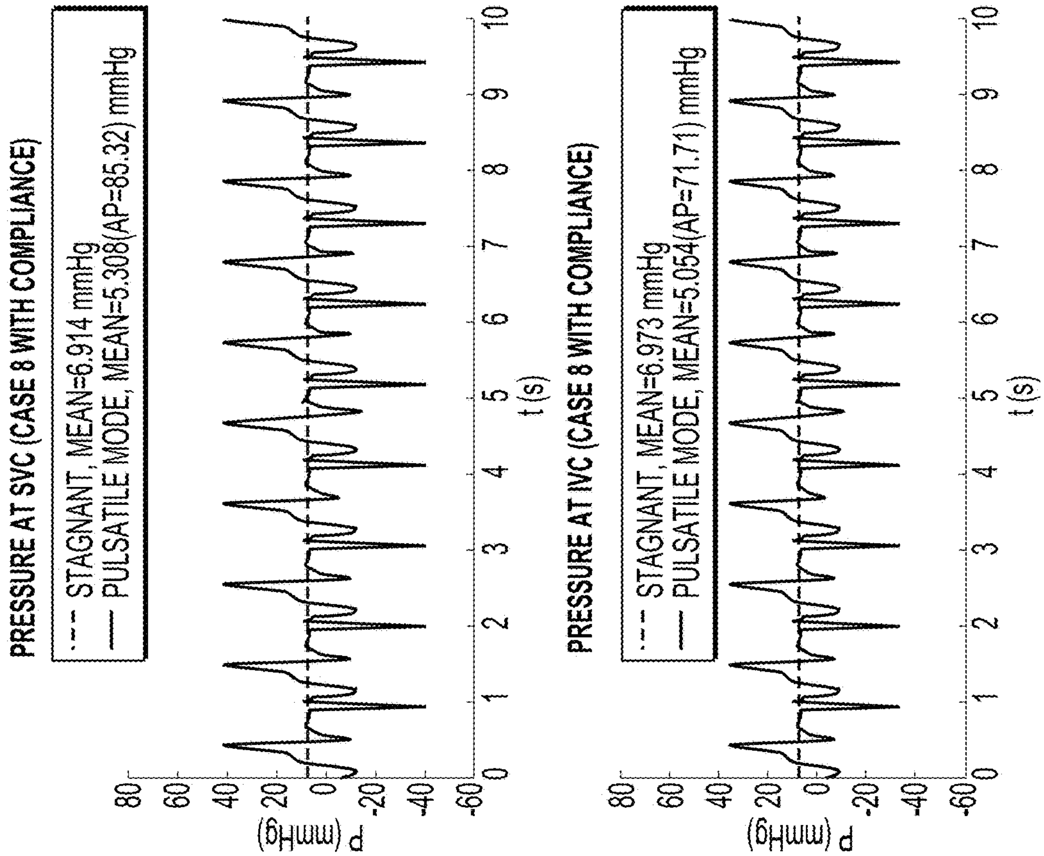
Figure 6J:
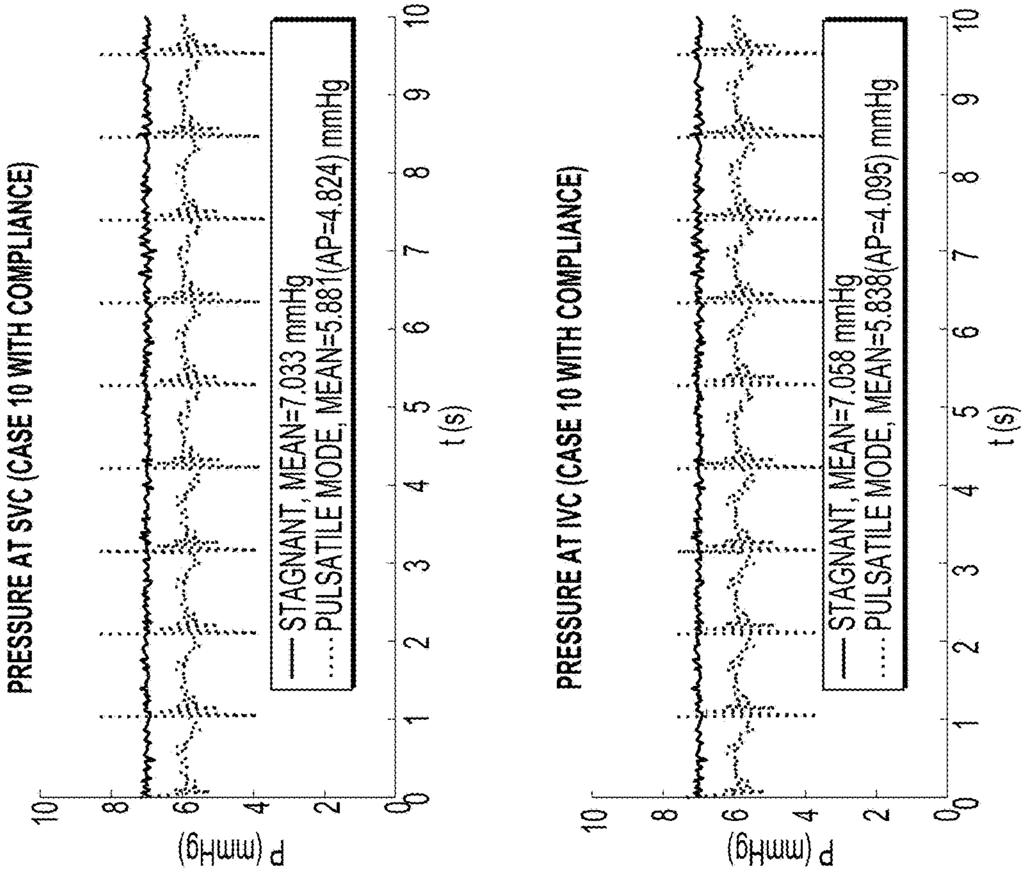
Figure 6I:
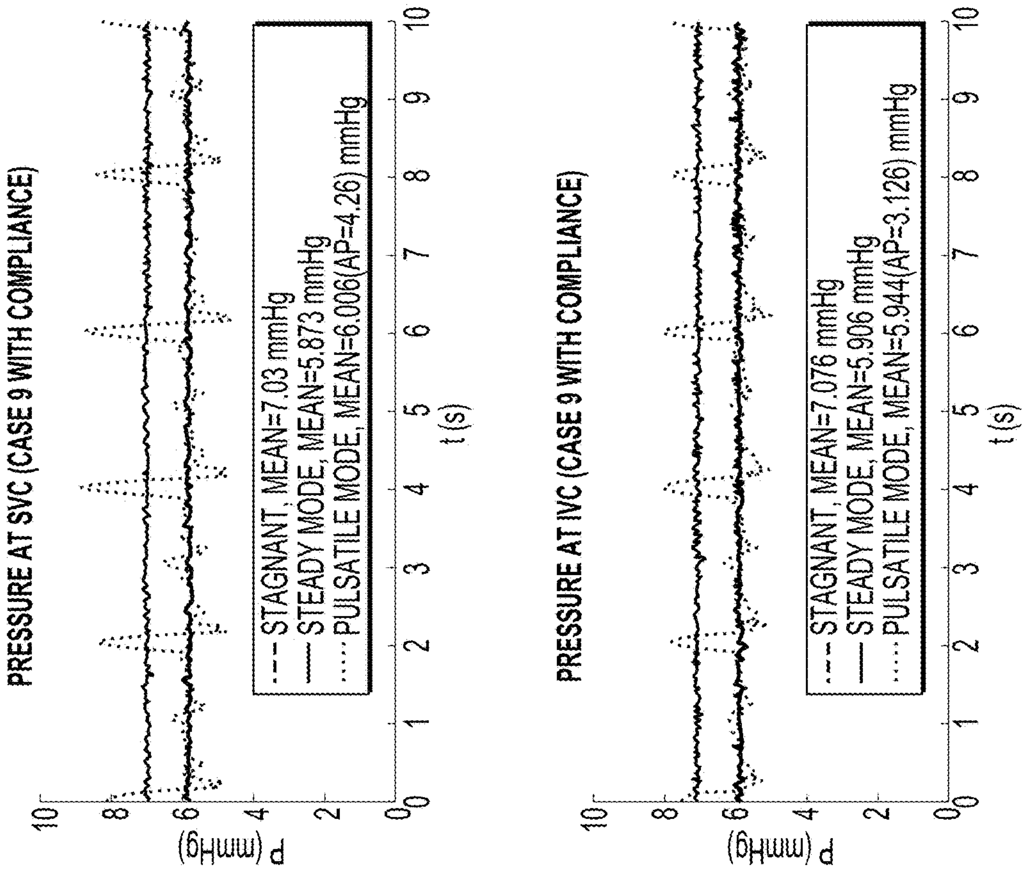
Figure 7C:
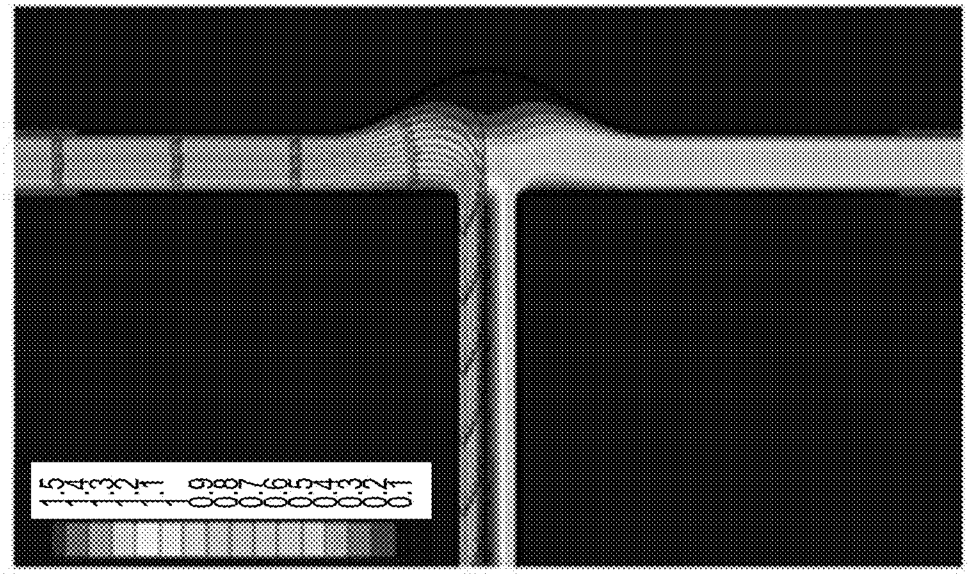
Figure 7B:
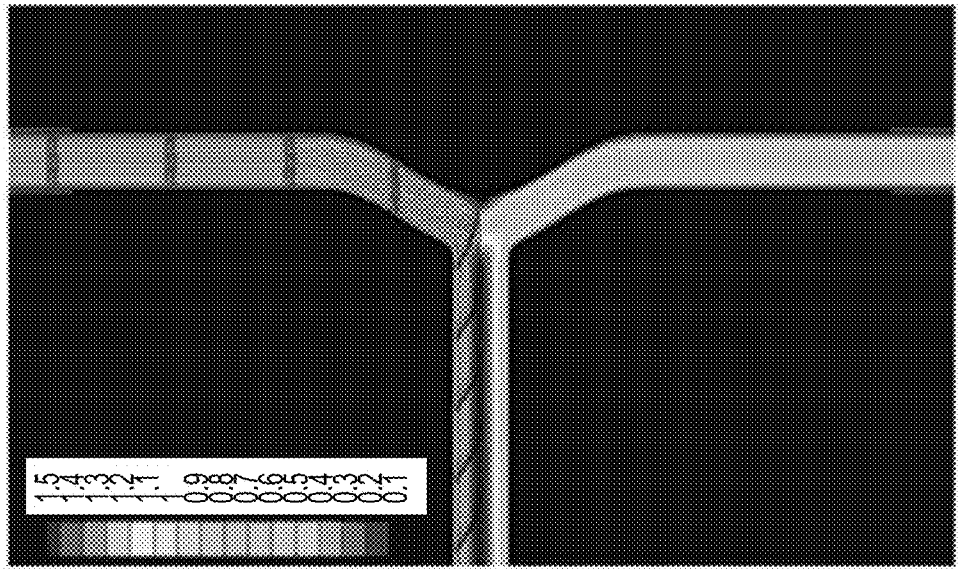
Figure 7A:
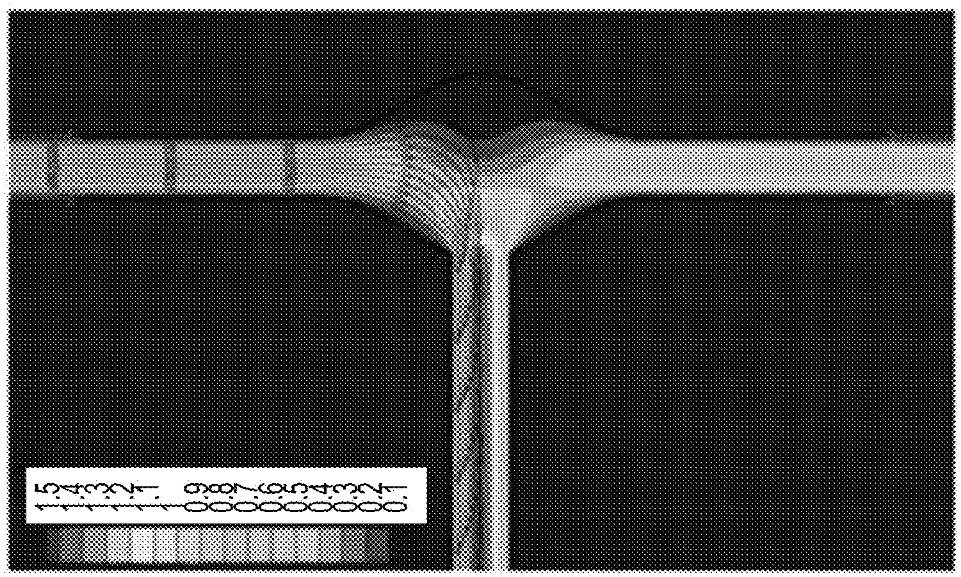
Figure 7F:
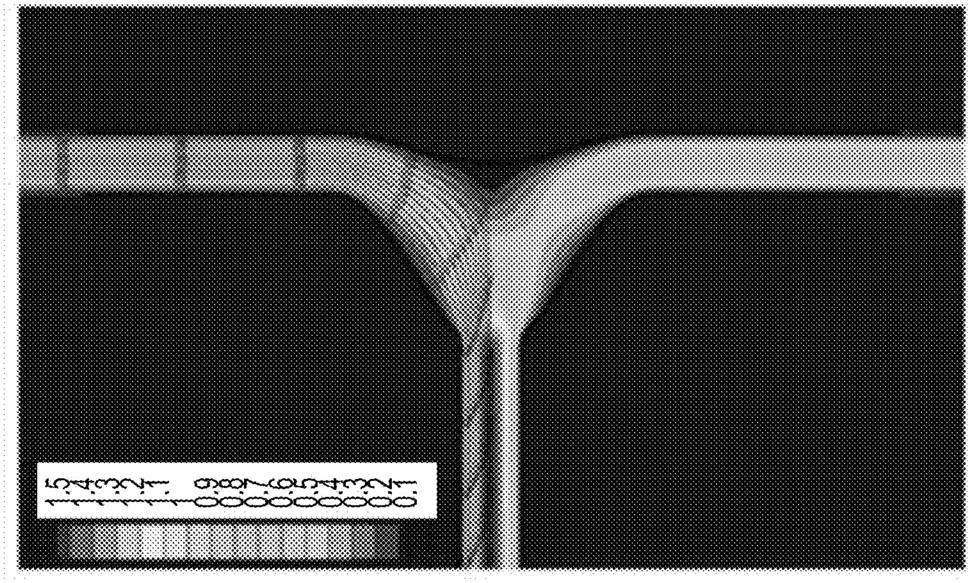
Figure 7E:
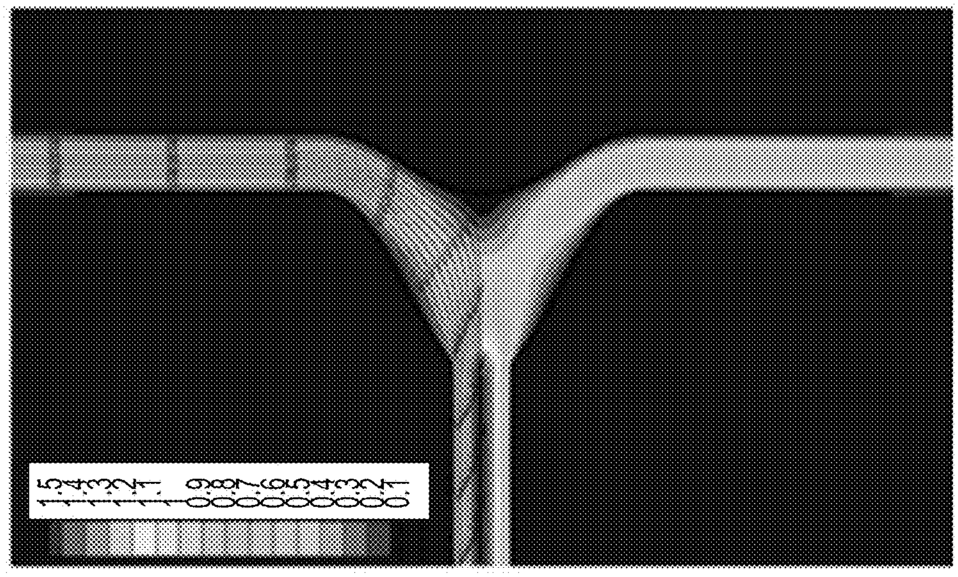
Figure 7D:
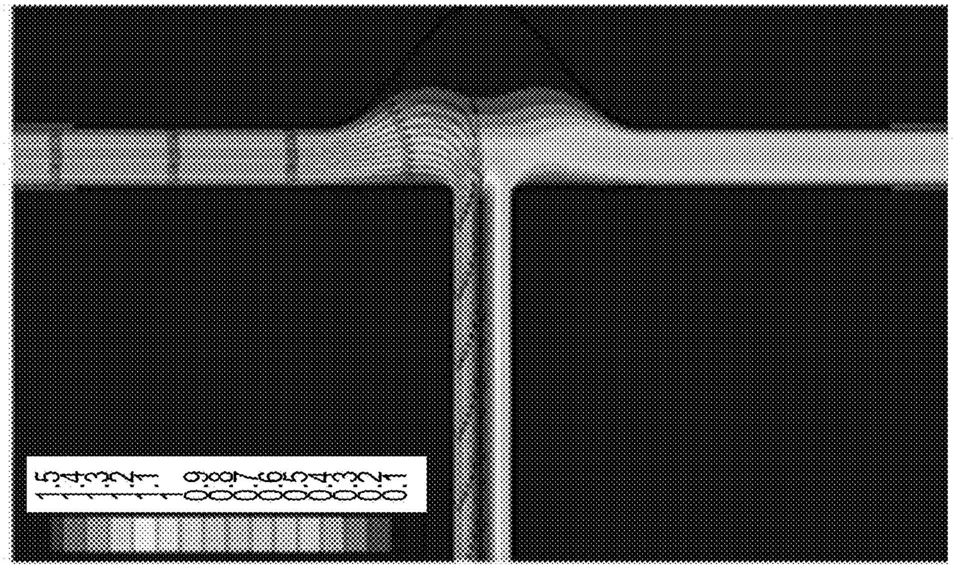

Example 10 (Comparative)—As shown in FIG. 5J, case 10 is similar to case 7 where the chamber is composed of a non-rigid material, such as silicon or latex.

Results

FIGS. 6A-J show the first conduit (FC) 14 and the second conduit (SC) 16 simulated pressure results of cases 1-10, respectively. The FC mean, FC pulse pressure, SC mean, and SC pulse pressure results are also shown in Table 1.

TABLE 1

Mean and pulse pressure results of cases 1-10

| Cases | FC mean (mmHg) | FC PP (mmHg) | SC mean (mmHg) | SC PP (mmHg) |
|---|---|---|---|---|
| Case 1 | 5.97 | 0.94 | 6.07 | 0.87 |
| Case 2 | 5.45 | 19.98 | 5.55 | 19.03 |
| Case 3 | 5.48 | 22.01 | 5.66 | 21.88 |
| Case 4 | 5.54 | 23.24 | 5.58 | 22.57 |
| Case 5 | 5.68 | 17.85 | 5.43 | 13.32 |
| Case 6 | 5.60 | 17.51 | 5.66 | 13.04 |
| Case 7 | 4.78 | 91.99 | 4.63 | 73.68 |
| Case 8 | 5.31 | 85.32 | 5.05 | 71.71 |
| Case 9 | 6.01 | 4.26 | 5.94 | 3.13 |
| Case 10 | 5.88 | 4.82 | 5.34 | 4.10 |

Computational fluid dynamic (CFD) tools, such as using Lattice-Boltzmann (LB) method using equations 1-6, below, were conducted on various geometries to find an optimal chamber 20 size. The results indicate that the geometry of FIG. 2F produced the lowest particle residence time while preserving the total volume within chamber 20. FIGS. 7A-F shows samples of simulated flow results corresponding to each of the FIGS. 2A-F and 3A-F. Table 2 demonstrates the particle residence time in various geometries. In LB method, Bhatnagar-Gross-Krook (BGK) is described as:

$$f_i(\boldsymbol{x}+\boldsymbol{e}_i\Delta x,\, t+\Delta t) = f_i(\boldsymbol{x},\, t) + \Omega_i(\boldsymbol{x},\, t) \quad \text{(eq. 1)}$$

Where, $f_i$ is the particle velocity distribution function.

$$\Omega_i = -\frac{1}{\tau}\left[f_i(\boldsymbol{x},\, t) - f_i^{eq}(\boldsymbol{x},\, t)\right],\ \tau = \frac{3\mu}{\rho\Delta t} + \frac{1}{2} \quad \text{(eq. 2)}$$

$\Omega_i$: the collision operator, τ: relaxation time μ: viscosity.

$$\rho = \sum_i f_i,\ \rho u = \sum_i f_i \boldsymbol{e}_i \quad \text{(eq. 3)}$$

Carreau-Yasuda model (blood):

$$\mu = (\mu_0 - \mu_\infty)\left[1 + (\lambda\dot{\gamma})^a\right]^{\frac{n-1}{a}} + \mu_\infty \quad \text{(eq. 4)}$$

The rate-of-strain tensor is defined as:

$$S_{\alpha\beta} = \frac{1}{2}\left(\frac{\partial u_\beta}{\partial x_\alpha} + \frac{\partial u_\alpha}{\partial x_\beta}\right) \quad \text{(eq. 5)}$$

The shear rate is defined as:

$$\dot{\gamma} = \sqrt{2\sum_{\alpha,\beta} S_{\alpha,\beta} S_{\alpha,\beta}} \quad \text{(eq. 6)}$$

TABLE 2

| Average particle residence time in various geometries | | | |
|---|---|---|---|
| FIG. 2 | $PRT_{ave}$ (unitless) | FIG. 3 | $PRT_{ave}$ (unitless) |
| (a) | 10.80 | (a) | 11.59 |
| (b) | 7.56 | (b) | 10.01 |
| (c) | 9.55 | (c) | 12.18 |
| (d) | 11.50 | (d) | 14.81 |
| (e) | 8.90 | (e) | 10.73 |
| (f) | 8.82 | (f) | 11.31 |

The description of the inventions herein in their many embodiments is merely exemplary in nature and, thus, variations that do not depart from the gist of the invention are intended to be within the scope of the invention. Such variations are not to be regarded as a departure from the spirit and scope of the invention.

What is claimed is:

1. A system for providing pulmonary support comprising:
- a chamber defined by a first conduit, a second conduit, a third conduit, and a wall;
- a first pump connected to the third conduit, and connected to a fourth conduit; and
- a second pump connected to a fifth conduit, and connected to a sixth conduit;
- wherein the chamber is configured to receive fluid via the first conduit and the second conduit;
- wherein the first pump is configured to receive fluid from the chamber via the third conduit;
- wherein the fourth conduit is configured to transport fluid from the first pump to a pulmonary artery;
- wherein the fifth conduit is configured to transport fluid from an oxygenated blood source to the second pump, wherein the oxygenated blood source is chosen from one of a pulmonary vein, a left atrium, and a left ventricle; and
- wherein the sixth conduit is configured to transport fluid from the second pump to an aorta.

2. The system of claim 1, wherein the wall has a concave surface.

3. The system of claim 1, wherein the chamber includes a convex surface and the wall has a concave surface.

4. The system of claim 1, wherein the chamber includes at least one convex surface.

5. A system for providing pulmonary support comprising:
- a chamber defined by a first conduit, a second conduit, a third conduit, and a wall; and
- a first pump connected to the third conduit, and connected to a fourth conduit;
- wherein the chamber is configured to receive fluid via the first conduit and the second conduit;
- wherein the first pump is configured to receive fluid from the chamber via the third conduit; and
- wherein the fourth conduit is configured to transport fluid from the first pump to a pulmonary artery;
- wherein the chamber includes a convex surface and the wall has a concave surface; and
- wherein a ratio of a diameter of the convex surface to the concave surface is from about 0.0:4 to about 4:0.0.

6. A system for providing pulmonary support comprising:
- a chamber defined by a first conduit, a second conduit, a third conduit, and a wall; and
- a first pump connected to the third conduit, and connected to a fourth conduit;
- wherein the chamber is configured to receive fluid via the first conduit and the second conduit;
- wherein the first pump is configured to receive fluid from the chamber via the third conduit; and
- wherein the fourth conduit is configured to transport fluid from the first pump to a pulmonary artery;
- wherein the chamber has a volume of from about 0 cc to about 110 cc.

7. The system of claim 6, wherein the chamber has a volume of from 0.1 cc to about 50 cc.

8. The system of claim 7, wherein the chamber includes a convex surface and the wall has a concave surface.

9. A system for providing pulmonary support comprising:
- a chamber defined by a first conduit, a second conduit, a third conduit, and a wall; and
- a first pump connected to the third conduit, and connected to a fourth conduit;
- wherein the chamber is configured to receive fluid via the first conduit and the second conduit;
- wherein the first pump is configured to receive fluid from the chamber via the third conduit; and
- wherein the fourth conduit is configured to transport fluid from the first pump to a pulmonary artery;
- wherein the chamber is made of a material that is capable of withstanding a pressure of from about 0 mm Hg to about 10 mm Hg.

10. A system for providing pulmonary support comprising:
- a chamber defined by a first conduit, a second conduit, a third conduit, and a wall; and
- a first pump connected to the third conduit, and connected to a fourth conduit;
- wherein the chamber is configured to receive fluid via the first conduit and the second conduit;
- wherein the first pump is configured to receive fluid from the chamber via the third conduit; and
- wherein the fourth conduit is configured to transport fluid from the first pump to a pulmonary artery;
- wherein the chamber is configured to expand from about 0.5% to about 50% in volume relative to an original size of the chamber.

11. The system of claim 10, wherein the chamber is made of a material chosen from polyester, polytetrafluoroethylene, and a combination thereof.

12. A system for providing pulmonary support comprising:
- a chamber defined by a first conduit, a second conduit, a third conduit, and a wall; and
- a first pump connected to the third conduit, and connected to a fourth conduit;
- wherein the chamber is configured to receive fluid via the first conduit and the second conduit;
- wherein the first pump is configured to receive fluid from the chamber via the third conduit; and
- wherein the fourth conduit is configured to transport fluid from the first pump to a pulmonary artery;
- wherein the chamber includes an interior surface with a coating.

13. A system for providing pulmonary support comprising:
- a chamber defined by a first conduit, a second conduit, a third conduit, and a wall; and
- a pump connected to the third conduit, and connected to a fourth conduit;
- wherein the chamber is configured to receive fluid via the first conduit and the second conduit;
- wherein the pump is configured to receive fluid from the chamber via the third conduit; and wherein the fourth conduit is configured to transport fluid from the pump to a pulmonary artery;

wherein each of the first conduit, the second conduit, and the third conduit includes at least one valve.

14. The system of claim 13, wherein the chamber includes a convex surface and the wall has a concave surface.

15. The system of claim 13, wherein the pump is a pressure-source pump or a flow-source pump.

16. A method for using a system for providing pulmonary support in a patient in need thereof, the method comprising:

attaching the system, wherein the system includes a chamber defined by a first conduit, a second conduit, a third conduit, and a wall; a first pump connected to the third conduit, and connected to a fourth conduit; and a second pump connected to a fifth conduit, and connected to a sixth conduit;

wherein the attaching of the system includes attaching the fourth conduit to a pulmonary artery and attaching the fifth conduit to an oxygenated blood source;

wherein the chamber receives fluid via the first conduit and the second conduit, the first conduit being attached to a superior vena cava and the second conduit being attached to an inferior vena cava;

wherein the first pump receives fluid from the chamber via the third conduit;

wherein the fourth conduit transports fluid from the first pump to the pulmonary artery;

wherein the fifth conduit transports fluid from the oxygenated blood source to the second pump, wherein the oxygenated blood source is chosen from one of a pulmonary vein, a left atrium, and a left ventricle; and wherein the sixth conduit transports fluid from the second pump to an aorta.

17. A method for using a system for providing pulmonary support in a patient in need thereof, the method comprising:

attaching the system, wherein the system includes a chamber defined by a first conduit, a second conduit, a third conduit, and a wall; and a first pump connected to the third conduit, and connected to a fourth conduit;

wherein the attaching of the system includes attaching the fourth conduit to a pulmonary artery;

wherein the chamber receives fluid via the first conduit and the second conduit, the first conduit being attached to a superior vena cava and the second conduit being attached to an inferior vena cava;

wherein the first pump receives fluid from the chamber via the third conduit;

wherein the fourth conduit transports fluid from the first pump to the pulmonary artery; and wherein the chamber has a volume of from about 0 cc to about 110 cc.

18. A method for using a system for providing pulmonary support in a patient in need thereof, the method comprising:

attaching the system, wherein the system includes a chamber defined by a first conduit, a second conduit, a third conduit, and a wall; and a first pump connected to the third conduit, and connected to a fourth conduit;

wherein the attaching of the system includes attaching the fourth conduit to a pulmonary artery, wherein the chamber receives fluid via the first conduit and the second conduit, the first conduit being attached to a superior vena cava and the second conduit being attached to an inferior vena cava;

wherein the first pump receives fluid from the chamber via the third conduit;

wherein the fourth conduit transports fluid from the first pump to the pulmonary artery;

wherein the chamber includes a convex surface and the wall has a concave surface; and wherein a ratio of a diameter of the convex surface to the concave surface is from about 0.0:4 to about 4:0.0.

19. A method for using a system for providing pulmonary support in a patient in need thereof, the method comprising:

attaching the system, wherein the system includes a chamber defined by a first conduit, a second conduit, a third conduit, and a wall; and a first pump connected to the third conduit, and connected to a fourth conduit;

wherein the attaching of the system includes attaching the fourth conduit to a pulmonary artery;

wherein the chamber receives fluid via the first conduit and the second conduit, the first conduit being attached to a superior vena cava and the second conduit being attached to an inferior vena cava;

wherein the first pump receives fluid from the chamber via the third conduit;

wherein the fourth conduit transports fluid from the first pump to the pulmonary artery; and wherein the chamber is made of a material that withstands a pressure of from about 0 mm Hg to about 10 mm Hg.

20. A method for using a system for providing pulmonary support in a patient in need thereof, the method comprising:

attaching the system, wherein the system includes a chamber defined by a first conduit, a second conduit, a third conduit, and a wall; and a first pump connected to the third conduit, and connected to a fourth conduit;

wherein the attaching of the system includes attaching the fourth conduit to a pulmonary artery, wherein the chamber receives fluid via the first conduit and the second conduit, the first conduit being attached to a superior vena cava and the second conduit being attached to an inferior vena cava;

wherein the first pump receives fluid from the chamber via the third conduit;

wherein the fourth conduit transports fluid from the first pump to the pulmonary artery; and wherein the chamber expands from about 0.5% to about 50% in volume relative to an original size of the chamber.

21. A method for using a system for providing pulmonary support in a patient in need thereof, the method comprising:

attaching the system, wherein the system includes a chamber defined by a first conduit, a second conduit, a third conduit, and a wall; and a first pump connected to the third conduit, and connected to a fourth conduit;

wherein the attaching of the system includes attaching the fourth conduit to a pulmonary artery, wherein the chamber receives fluid via the first conduit and the second conduit, the first conduit being attached to a superior vena cava and the second conduit being attached to an inferior vena cava;

wherein the first pump receives fluid from the chamber via the third conduit;

wherein the fourth conduit transports fluid from the first pump to the pulmonary artery; and wherein the chamber includes an interior surface with a coating.

22. A method for using a system for providing pulmonary support in a patient in need thereof, the method comprising:

attaching the system, wherein the system includes a chamber defined by a first conduit, a second conduit, a third conduit, and a wall; and a first pump connected to the third conduit, and connected to a fourth conduit;

wherein the attaching of the system includes attaching the fourth conduit to a pulmonary artery, wherein the chamber receives fluid via the first conduit and the second conduit, the first conduit being attached to a superior vena cava and the second conduit being attached to an inferior vena cava;

wherein the first pump receives fluid from the chamber via the third conduit;

wherein the fourth conduit transports fluid from the first pump to the pulmonary artery; and wherein each of the first conduit, the second conduit, and the third conduit includes at least one valve.

* * * * *